(12) United States Patent
Shang

(10) Patent No.: US 10,918,881 B1
(45) Date of Patent: Feb. 16, 2021

(54) EXCHANGEABLE LASER AND ARRAY THEREOF

(71) Applicant: Hua Shang, Nanjing (CN)

(72) Inventor: Hua Shang, Nanjing (CN)

(73) Assignee: Hua Shang, Nanjing (CN)

( * ) Notice: Subject to any disclaimer, the term of this patent is extended or adjusted under 35 U.S.C. 154(b) by 0 days.

(21) Appl. No.: 16/849,572

(22) Filed: Apr. 15, 2020

Related U.S. Application Data

(63) Continuation of application No. PCT/CN2019/105121, filed on Sep. 10, 2019.

(30) Foreign Application Priority Data

Aug. 13, 2019 (CN) .......................... 2019 1 0745329

(51) Int. Cl.
*A61N 5/06* (2006.01)
*G02B 6/42* (2006.01)
*H05K 7/14* (2006.01)
*H01S 3/23* (2006.01)
*A61N 5/067* (2006.01)

(52) U.S. Cl.
CPC .............. *A61N 5/06* (2013.01); *A61N 5/062* (2013.01); *G02B 6/4215* (2013.01); *G02B 6/4292* (2013.01); *H01S 3/2391* (2013.01); *H05K 7/1401* (2013.01); *A61N 2005/067* (2013.01)

(58) Field of Classification Search
None
See application file for complete search history.

(56) References Cited

U.S. PATENT DOCUMENTS

| 5,345,707 A * | 9/1994 | Randall ..................... F41G 1/35 362/110 |
| 5,594,753 A * | 1/1997 | Frey .......................... H01S 3/03 372/57 |
| 2017/0353005 A1* | 12/2017 | Filgas ................... H01S 3/0407 |

FOREIGN PATENT DOCUMENTS

| CN | 110429455 A | * 11/2019 |
| CN | 110445008 A | * 11/2019 |
| KR | 101656227 B1 | * 9/2016 |

* cited by examiner

*Primary Examiner* — Michael Stahl
(74) *Attorney, Agent, or Firm* — Andrus Intellectual Property Law, LLP

(57) ABSTRACT

Disclosed is an exchangeable laser and an array thereof. The exchangeable laser includes a cartridge receiver having a uniform shape and a uniform electrical interface, and including laser elements inside thereof, and a housing for clamping a cartridge receiver. The power supply and parameter controls of the laser element are realized by cylindrical protrusions with a certain degree of inclination on clip-lock panel and electronic interfaces within cylindrical slots of the cartridge receiver, and the cylindrical protrusions and cylindrical slots with the certain degree of inclination can realize precise positioning of the cartridge receiver and the housing. In the exchangeable laser array of the disclosure, the cartridge receiver inside each housing can be replaced by other cartridge receiver that emits laser with a different wavelength, and the plurality of housings can be connected with a plurality of wavelength switchers in the back to realize selective output of the wavelength.

19 Claims, 12 Drawing Sheets

EXCHANGEABLE LASER AND ARRAY THEREOF

CROSS REFERENCE TO RELATED APPLICATIONS

This application is a bypass continuation of International Patent Application No. PCT/CN2019/105121 filed on Sep. 10, 2019, which claims priority to Chinese patent application No. CN201910745329.3, filed on Aug. 13, 2019, contents of both of which are incorporated herein by reference in their entireties.

TECHNICAL FIELD

The present disclosure relates to the technical field of laser medical instruments, in particular relates to an exchangeable laser and an array thereof for photodynamic therapy.

BACKGROUND

Photodynamic Therapy (PDT) is a new technology for the diagnosis and treatment of diseases by using a photodynamic effect. This therapy is based on the photodynamic effect. It belongs to a photosensitization reaction with biological effects in which oxygen molecule is involved, and comprises the following processes: a photosensitizer absorbed by a tissue is excited by the irradiation of a specific wavelength of laser; and then energies of the photosensitizer in the excited state are transferred to oxygen in the surrounding environment, to generate highly active singlet oxygen; the singlet oxygen and adjacent biomacromolecules occur oxidation reaction, and thus produce cytotoxicity, which in turn leads to cell damage or even death. Compared with traditional therapies, photodynamic therapy has many advantages including small trauma, good targeting, no drug resistance and side effects.

Laser is the most convenient and portable light source, and has coherence and mono-chromaticity. That is, a laser source can produce a single wavelength of light with the high energy. In addition, an output power of the laser source can be precisely regulated, and laser produced thereby can be directly introduced into hollow organs, penetrating into tumors through fiber optical cables. The photodynamic treatment time is related to the light absorbing ability of the photosensitizers and the effectiveness of energy transfer between light and oxygen. The laser wavelength and the required energy are variable depending on the indications being treated and the type of photosensitizer. Most of photosensitizers strongly absorb light with a wavelength of 630 nm or greater than 630 nm. For example, Photofrin is a photosensitizer used for gastric cancer and bladder cancer, and has an excitation wavelength of 630 nm; Metvix is a photosensitizer used for basal cell carcinoma, and has an excitation wavelength of 635 nm; Foscan is a photosensitizer used for head and neck tumors, and has an excitation wavelength of 652 nm; Purlytin is a photosensitizer used for breast cancer and prostate cancer, and has an excitation wavelength of 664 nm; Talaporfin is a broad spectrum photosensitizer used for solid tumors, and has an excitation wavelength of 664 nm; Verteporfin is a photosensitizer used for basal cell carcinoma, and has an excitation wavelength of 689 nm; Lutex is a photosensitizer used for prostate cancer and brain cancer, and has an excitation wavelength of 732 nm. For photodynamic therapy, there are many types of photosensitizers and applicable diseases, and new types of photosensitizers are constantly being introduced in the market. When replacing lasers or replacing the wavelength of laser, medical personnel who do not have common knowledge in the field of lasers are at a loss or prone to making mistakes.

Moreover, the lasers have a complicated structure, high price, and the use thereof is cumbersome. In particular, the lasers used in the photodynamic therapy instruments are semiconductor lasers which not only require to be powered by an external power supply, but also to adjust and control many parameters including the power, wavelength and pulse. Due to various devices for externally-supplying power or controlling parameters, it is necessary to rely on a number of external power connectors for communication. And a slight accident will cause connection errors, so that medical personnel feel fearful when using medical lasers (especially when replacing lasers), which seriously hinders the popularization of laser therapeutic instruments in the medical filed.

SUMMARY

In view of the above, an object of the present disclosure is to provide an exchangeable laser capable of quickly and accurately switching laser elements that can produce lights with different wavelengths, and an array thereof.

An exchangeable laser is provided. The exchangeable laser includes a cartridge receiver in which a laser element is fixed and a housing for clamping the cartridge receiver. The cartridge receiver has one electrical interface and several optical interfaces for interfacing with the housing. The cartridge receiver can be withdrawn from the housing and replaced with another cartridge receiver including a laser element that emits laser of different wavelength. The laser element may be a semiconductor laser element, a solid laser element, a gas laser element or other kinds of laser elements. A diode laser element is preferred as it is cheaper than a metal-vapor laser element or a tuned-dye laser element and is portable.

Specifically, the housing includes a first accommodating space for accommodating the cartridge receiver, a clamping unit, and a second accommodating space for accommodating the clamping unit. A front panel of the housing is provided with an insertion port for a horizontal insertion of the cartridge receiver into the first accommodating space.

The second accommodating space is disposed below the first accommodating space and is communication with the first accommodating space through a clamping port provided on a bottom panel of the first accommodating space.

The clamping unit includes a clip-lock assembly and a button assembly. The clip-lock assembly includes a clip-lock panel disposed horizontally and an elastic assembly disposed under the clip-lock panel.

An upper panel of the clip-lock panel is provided with a plurality of cylindrical protrusions with axes inclined rearward, and a lower panel corresponding to the upper panel of the cartridge receiver is provided with a plurality of cylindrical slots having a same shape as the cylindrical protrusions. Male and female electrical interfaces are respectively provided inside the cylindrical protrusions and cylindrical slots. The cylindrical protrusions pass upward through the clamping port and clamp the cylindrical slots under an action of the elastic assembly, so as to power the laser element and assist in adjusting parameters of the laser element. Preferably, the electrical interfaces of cylindrical protrusions are connected with a power supply and/or a parameter control device for adjusting the laser element.

Electrical interfaces of the cylindrical slots are respectively connected to a port of the power supply and/or parameter control interfaces including an interface for adjusting power, an interface for adjusting wavelength, and an interface for adjusting a pulse.

When the button assembly moves backward, the clip-lock panels are driven to move obliquely downward along an axial direction of the cylindrical protrusions until the cylindrical protrusions disengage from the cylindrical slots, thereby causing the cartridge receiver to be disengaged from the clip-lock panel. This facilitates the withdrawal of the cartridge receiver from the insertion port and the arrangement of other cartridge receiver having a laser element that emits laser of different wavelength. That is, the switching of the wavelength of the laser can be completed by simply switching the cartridge receiver.

When the other cartridge receiver is arranged into the first accommodating space and the button assembly is reset forward, the clip-lock panel is moved obliquely upward along the axial direction of the cylindrical protrusions under the action of the elastic assembly, until the cylindrical protrusions engage with the cylindrical slots, thereby powering the laser element and/or performing the adjustment of laser element parameters.

Preferably, a back panel of the housing is provided with an optical joint at a position of the back panel horizontally corresponding to a position of the insertion port, and the cartridge receiver is provided with an optical interface at a position corresponding to the optical joint. The cartridge receivers that include different laser elements emitting laser of different wavelength have a unified optical interface and electrical interface, which greatly reduces the difficulty for medical personnel to switch laser wavelengths, and improves the popularization of laser therapeutic instruments in the medical field.

The optical interface of the cartridge receiver includes a tapered cavity with a cone top at front and an axis extending rearward. A small cylindrical cavity is arranged extending horizontally forwardly from the cone top of the tapered cavity and is communication with the tapered cavity; a big cylindrical cavity is arranged extending horizontally backwardly from a cone bottom of the tapered cavity. A front side of the small cylindrical cavity is directly connected a laser output of the laser element, or is connected to the laser output of the laser element through an optical fiber ferrule.

The back panel of the housing is provided with an optical joint (i.e., an optical connector) capable of matching with the optical interface of the cartridge receiver. The optical joint includes a tapered adapter having a same shape as the tapered cavity, and an external optical fiber disposed inside the tapered adapter. A front end of the external optical fiber is provided with an external optical fiber ferrule capable of inserting into the small cylindrical cavity. The external optical fiber ferrule is arranged at a front end of the tapered adapter, a cylindrical adapter with a same shape as the large cylindrical cavity is arranged extending forwardly from a back end of the tapered adapter. The cylindrical adapter extends to be flush with the back panel of the housing.

A top portion of the optical fiber ferrule has a lens, and the lens is a convex lens or a lenticular lens or a graded-index lens. When the optical interface is mated with the optical joint, a distance between a front end face of an optical fiber of the external optical fiber ferrule and the lens is equal to a focal length of the lens.

Preferably, the tapered cavity has a taper angle of 45°.

Preferably, the clamping unit further includes a clamping box, and the clamping box is fixed to the second accommodating space. In addition, a lower portion of the elastic assembly is fixed to a bottom of the clamping box. When the clip-lock panel is moved up and down, the clip-lock panel is not completely detached from the clamping box. A left and right sides of the clamping box are provided with a plurality of inclined rails having a same inclination degree as the axis of the cylindrical protrusion, and a left and right sides of the clip-lock panel corresponding to the clamping box, are provided with inclined guide channels.

Preferably, a left and right side surfaces of the second accommodating space are provided with a plurality of inclined guide rails having a same inclination degree as the axis of the cylindrical protrusion, and a left and right sides of the clip-lock panel corresponding to the second accommodating space are provided with inclined guide channels. In addition, the lower portion of the elastic assembly is fixed to a bottom of the second accommodating space. When the clip-lock panel is moved up and down, the clip-lock panel is not completely detached from the inclined guide rails.

Preferably, the button assembly includes a release button arranged at the front panel of the housing corresponding to the second accommodating space, and a frame connector arranged behind the release button. A vertical strip-shaped slot is provided backside of the release button, and an inclined strip-shaped slot is provided frontside of the clip-lock panel. The vertical strip-shaped slot and the inclined strip-shaped slot have openings oriented perpendicular to left and right panels of the housing, respectively. An inclined direction of the inclined strip-shaped slot is perpendicular to the axis of the cylindrical protrusion. An upper rod and lower rod of the frame connector are respectively capable of sliding in the inclined strip-shaped slot and the vertical strip-shaped slot. A left rod and right rod of the frame connector are horizontally hinged to the left and right panels of the clamping box, respectively. When the release button moves backward, the vertical strip-shaped slot moves backward, which allows the lower rod of the frame connector rotating obliquely backward in the vertical strip-shaped slot, and in turn allows the upper rod of the frame connector rotating obliquely forward in the inclined strip-shaped slot. At the same time, a force direction of the inclined strip-shaped slot is always the same as an inclination direction of the cylindrical protrusion, which allows the clip-lock panel to move downward along the inclination direction of the cylindrical projection.

Preferably, the clip-lock panels further include buckles disposed on the upper portion of the clip-lock panel and located in front of the cylindrical protrusions, and a buckle slot is provided under the corresponding lower panel of the cartridge receiver at positions corresponding to positions of the buckles. When the back panel of the cartridge receiver is connected with the back panel of the housing, the buckle exactly clamp the buckle slot, and the male and female electrical interfaces inside the cylindrical protrusion and the cylindrical slots corresponding to the cylindrical protrusion are connected with each other.

Preferably, the first accommodating space and the cartridge receiver have a same shape. The left panel and the right panel of the cartridge receiver are provided with horizontal positioning grooves, and the left panel and the right panel of the first accommodating space corresponding to the left panel and the right panel of the cartridge receiver are provided with horizontal positioning protrusions; and/or a front portion of the left panel and the right panel of the cartridge receiver is provided with an anti-slip groove structure, and the insertion port further includes a plugging cartridge receiver groove for the cartridge receiver corresponding to the anti-slip groove structure in front of the left panel and right panel of the housing.

Preferably, an upper back portion of the cartridge receiver is further provided with a heat sink, and the upper panel of the housing is provided with a forced air cooling inlet at a position corresponding to a position of the heat sink. The left panel and/or the right panel of the housing are arranged with forced air cooling outlets, respectively.

Preferably, the cylindrical protrusions are arrayed on an upper surface of the clip-lock panel, and the cylindrical slots are arrayed on the lower panel of the cartridge receiver, corresponding to the array of the cylindrical protrusions. An angle between the axis of the cylindrical projection and a horizontal plane is 45°. That is to say, the axis of the cylindrical projection is inclined rearward by 45°.

An exchangeable laser array is provided. The exchangeable laser array includes at least two of the above-mentioned exchangeable lasers, and in each of the exchangeable lasers, a left side and right side of the housing are respectively provided with a horizontal guide channel array and a horizontal guide rail array.

Preferably, the exchangeable laser array further includes a wavelength switcher. The wavelength switcher includes a plurality of optical fiber input interfaces connected (directly or indirectly) to optical interfaces of exchangeable lasers of the exchangeable laser array, one optical fiber output interface, a base and a plurality of optical fiber plugs. The base includes a baseplate and a stationary shaft extending upward along a center of the baseplate. The stationary shaft is fixed with a drive gear and an optical fiber displacement disk that coincide with an axis of the stationary shaft from bottom to top. The optical fiber plugs include optical fiber plugging rods, a driven gear assembly disposed at periphery of the optical fiber plugging rods and meshing with the drive gear. One end of the optical fiber plugging rod is connected to the optical fiber input interface, and other end of the optical fiber plugging rod is actively connected to the optical fiber output interface. Preferably, a plurality of optical fiber plugging ports for positioning the optical fiber plugs are axisymmetrically disposed on the optical fiber displacement disk at a radial periphery of the drive gear. A plurality of output ports for spirally connecting the optical fiber output interfaces are disposed on the baseplate vertically corresponding to the optical fiber plugging ports.

Preferably, when the optical fiber plugging rods are located above the baseplate, the optical fiber displacement disk is rotated under an action of the drive gear and driven gear; when the optical fiber plugging rod is rotated to locate above the output port, the optical fiber plugging rods is moved up or down along the optical fiber plugging port under the action of the drive gear and driven gear, so as to pull out from the output port or insert into the optical fiber output port.

Preferably, the wavelength switcher further includes a micro-switch device disposed above the optical fiber displacement disk. The micro-switch device includes a micro-switchgear, and a plurality of micro-switch elements. Micro-switch positioning slots with the same angle as the optical fiber plugs are disposed on the optical fiber displacement disk. When the optical fiber displacement disk is rotated, a triggering unit of the micro-switch elements moves from one micro-switch positioning slot to an adjacent micro-switch positioning slot. At the same time, the optical fiber plug is moved from an upper position of one output port to an upper position of an adjacent output port. Specifically, the optical fiber plugging ports are axisymmetrically disposed on the optical fiber displacement disk, and micro-switch positioning slots are adaptively disposed in a radial direction of the fiber displacement disk in which the optical fiber plugging ports are located, so as to ensure that the optical fiber plug can be accurately positioned above the output ports when the optical fiber displacement disk is rotated.

Preferably, the driven gear is connected to the optical fiber plugging rods through a screw-nut pair. On the optical fiber plugging rods, lower portions of the optical fiber plugging rods are provided with vertical positioning slots matching with positioning protrusions of the optical fiber plugging ports. Upper portions of the vertical positioning slots are provided with a screw external thread matching with a screw internal thread of the driven gear.

Preferably, an upper portion of the screw external thread is provided with a spring and a spring positioning shoulder.

Preferably, an upper portion of the spring positioning shoulder is a fiber ferrule connected to the optical fiber output interface, and the fiber ferrule is in a tapered shape.

Preferably, the screw internal thread of the driven gear is longer than the screw external thread of the optical fiber plugging rod. When a top of the screw external thread abuts against a top of the screw internal thread, and/or when a bottom of the vertical positioning slot abuts against a bottom of the positioning protrusion, a bottom of the optical fiber plugging rod is located at least above the baseplate.

The present disclosure has the following advantages.

1. The exchangeable laser of the disclosure is composed of cartridge receivers having a uniform shape, a uniform electrical interface and optical interface and including laser elements inside thereof and a housing for clamping one of the cartridge receivers. The laser elements inside the cartridge receivers may be a semiconductor laser element, a solid laser element, a gas laser element or other kinds of laser elements. Laser is output through the same optical joint provided at the back of the housing. The power supply and parameter controls of the laser element can be realized by the electronic interfaces of the cylindrical protrusions with the inclined angles of the clip-lock panel and cylindrical slots of the cartridge receiver. In addition, the cylindrical protrusions with the inclined angles and cylindrical slots with the same inclined angles can realize the precise positioning of the housing and the cartridge receiver. When replacing one laser element by a laser element that emits laser with a different wavelength, it is only necessary to withdraw the current cartridge receiver from the housing, and replace it by another cartridge receiver that includes the laser element emitting laser with the different wavelength. Therefore, the replacement of the laser elements is converted to the replacement of cartridge receivers that include different laser elements emitting laser with different wavelengths, and have uniform shapes, uniform electrical interfaces and optical interfaces, which greatly reduces the difficulty for medical personnel to switch laser wavelengths, and improves the popularization of laser therapeutic instruments in the medical field.

2. In the exchangeable laser of the disclosure, the cartridge receiver adopts an optical interface with a tapered cavity and a cylindrical cavity, and an optical joint matching with optical interface is provided with a tapered adapter and cylindrical adapter, so that a precise mechanical connection can be achieved between the output of the laser elements of the cartridge receiver and the output of the optical fiber of the housing without professional tools, facilitating standardization of the output components of the laser elements of the cartridge receiver.

3. In the exchangeable laser of the disclosure, the clip-lock panels include mechanical buckles. The buckle is engaged with the buckle slot of the cartridge receiver to further prevent the cartridge receiver from coming out of the housing. This improves the security and stability of the system. In addition, the cartridge receiver has the anti-slip groove structure, which is convenient for the user to remove the cartridge receiver from the first accommodating space or insert the cartridge receiver into the first accommodating space of the housing, thereby laying a foundation for the extensive use in the medical field.

4. In the exchangeable laser array of the disclosure, housings have uniform optical fiber joints and electronic joints. The optical fiber joints of the housings are directly or indirectly connected to external optical fibers, and output lasers having multiple wavelengths, and output through different optical fibers to different instruments such as photodynamic therapy devices or dedicated wavelength switchers. When the photosensitizer needs to be replaced temporary during the treatment, it is only necessary to purchase a cartridge receiver that corresponds to the wavelength of the photosensitizer and insert it into the housing.

5. In the exchangeable laser array of the disclosure, the cartridge receiver inside the housing can be replaced by other cartridge receiver that emits laser with a different wavelength. The housings may be connected with wavelength switchers to realize wavelength selection output.

6. The exchangeable laser array of the disclosure further includes a wavelength conversion device for achieving the mechanical coupling and switching among the plurality of input optical fibers and one output optical fiber of the exchangeable laser. Through the relative positional change among the plurality of optical fiber plugs and the optical fiber output interface, when a certain input optical fiber is aligned with the optical fiber output interface, laser in the optical fiber connected to this optical fiber plug is output, so as to realize switching of different wavelength outputs. This means of switch is easy to learn and use, which further promotes the development of laser therapeutic instruments in the medical field.

7. In the exchangeable laser array of the disclosure, the wavelength conversion device controls the opening and closing of the micro-switch element by a micro-motion spring, a limiting ball and a micro-motion rod. The structure thereof is skillfully connected with the base and the optical fiber displacement disk, thereby achieving steering control of the drive gear and precise positioning of the optical fiber plugging rods.

8. In the exchangeable laser array of the disclosure, the wavelength conversion device can not only realize the output of lasers with different wavelengths by one optical fiber output interface, but also can realize the output of laser with same or different wavelengths by the plurality of optical fiber interfaces, thereby improving the efficiency of photodynamic therapeutic instrument.

9. In the exchangeable laser array of the disclosure, the wavelength conversion device uses a thread stop structure at an end of the screw external thread to prevent the screw internal thread from being screwed out, and/or the bottom of the vertical positioning slot of the optical fiber plugging rod abuts against the bottom of the vertical positioning protrusion of the optical fiber plugging port, so as to lock the up and down movement of the optical fiber plugging rod, and in turn to rotate the optical fiber displacement disk to drive the overall movement of the optical fiber insertion plug.

10. In the exchangeable laser array of the disclosure, the wavelength conversion device utilizes a spring disposed at bottom of the optical fiber plugging rod and a spring positioning shoulder, so that the optical fiber plugging rod can elastically insert into the optical fiber output interface, avoiding the damage of head portion of the optical fiber ferrules at the bottom. In addition, there is a downward force after insertion, so that the coupling between the fiber ferrules is tight enough without loosening.

Figure 1:
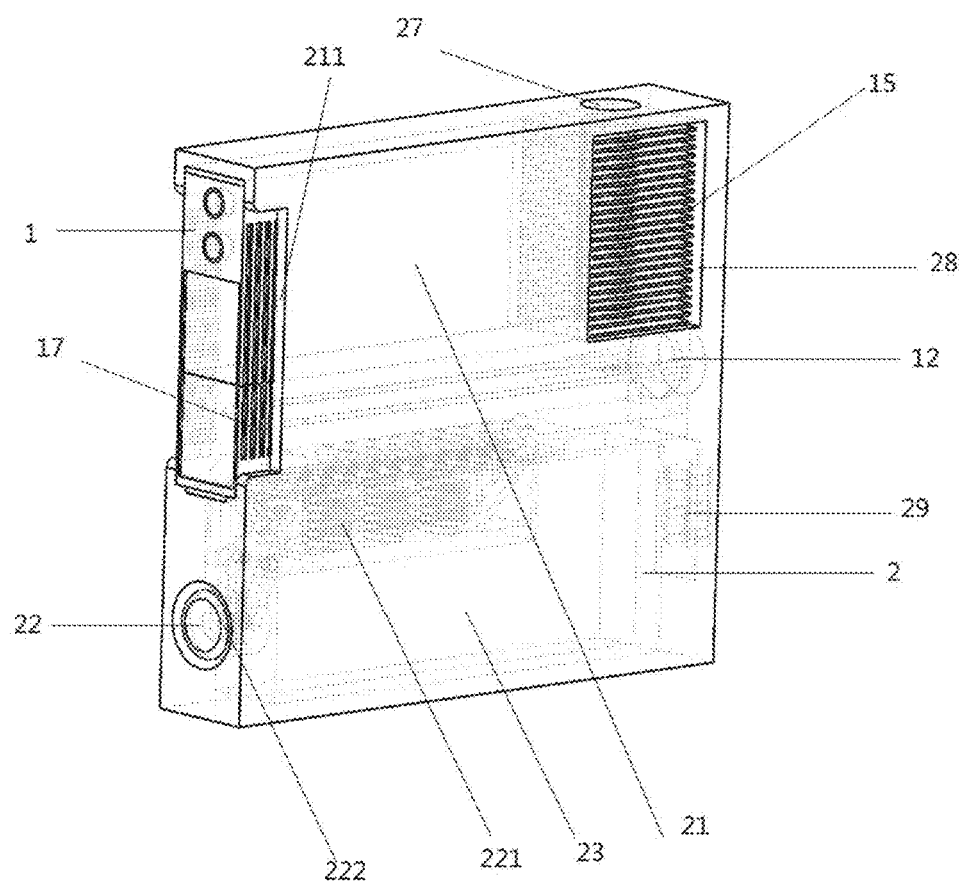
FIG. 1 is a three-dimensional schematic diagram illustrating the structure of the exchangeable laser according to example 1 of the disclosure.

LIST OF REFERENCE SYMBOLS 1, cartridge receiver; 11, electrical interface; 12, optical interface; 121, tapered cavity; 122, small cylindrical cavity; 123, large cylindrical cavity; 124, optical fiber ferrule; 125, convex lens; 13, cylindrical slot; 14, buckle slot; 15, heat sink; 151, cooling inlet for heat sink; 16, horizontal positioning groove; 17, anti-slip groove structure; 18, display device; 2, housing; 21, first accommodating space; 211, insertion port; 2111, plugging cartridge receiver groove; 212, clamping port; 213, horizontal positioning protrusion; 22, clamping unit; 221, clip-lock assembly; 2211, clip-lock panel; 22111, inclined guide groove; 2112, inclined strip-shaped groove; 2212, elastic assembly; 222, button assembly; 2221, release button; 2221a, vertical strip-shaped groove; 2222, frame connector; 22221, upper rod; 22222, lower rod; 22223, left rod; 22224, right rod; 223, clamping box; 2231, inclined guide rail; 23, second accommodating space; 24, cylindrical protrusion; 25, optical joint; 251, tapered adapter; 252, external optical fiber; 253, external optical fiber ferrule; 254, cylindrical adapter; 26, buckle; 27, forced air cooling inlet; 28, forced air cooling outlet; 29, electrical input joint; 3, wavelength switcher; 31, optical fiber input interface; 32, optical fiber output interface; 33, base; 331, baseplate; 3311, output port; 332, stationary shaft; 34, optical fiber plug; 341, optical fiber plugging rod; 3411, vertical positioning groove; 342, driven gear; 3421, screw-nut pair; 3422, optical fiber plugging rod bearing; 343, spring; 344, spring positioning shoulder; 35, drive gear; 36, optical fiber displacement disk; 361, optical fiber plugging port; 362, micro-switch positioning slot; 37, micro-switch device; 371, micro-switchgear; 3711, micro-slot; 372, micro-switch element; 373, micro-motion spring; 374, limiting ball; 375, micro-motion rod

DETAILED DESCRIPTION

Reference will now be made in detail to exemplary embodiments, examples of which are illustrated in the accompanying drawings, in order to facilitate the understanding of the disclosure. The following description and the accompanying drawings only show preferred embodiments, and the disclosure may be embodied in many different forms and not limited to the embodiments described herein. Rather, these embodiments are provided for fully understanding of the present disclosure. In particular, the directional terms used in the disclosure, such as "upper", "lower", "before", "after", "left", "right", "inside", "outside", "side" are only referred to the orientation in accompanying drawings. It should be understand that the directional terms are used to illustrate the disclosure, and are not intended to limit the disclosure.

Example 1

As shown in FIGS. 1-10, an exchangeable laser is provided. The exchangeable laser includes a cartridge receiver 1 in which a laser element is fixed and a housing 2 for clamping the cartridge receiver 1. The cartridge receiver 1 has one electrical interface 11 and several optical interfaces 12 for docking with the housing 2. The cartridge receiver 1 can be withdrawn from the housing 2 and replaced by another cartridge receiver including a laser element that emits laser of different wavelength.

Specifically, the housing 2 includes a first accommodating space 21 for accommodating the cartridge receiver 1, a clamping unit 22, and a second accommodating space 23 for accommodating the clamping unit. A front panel of the housing 2 is provided with an insertion port 211 for horizontally inserting the cartridge receiver 1 into the first accommodating space 21. The cartridge receiver 1 is detached and replaced via the insertion port 211. The second accommodating space 23 is disposed below the first accommodating space 21 and is communication with the first accommodating space 21 through a clamping port 212 provided on a bottom panel of the first accommodating space 21. Since there are many drawings in the disclosure, the word "front" refers to the position of the insertion port when the cartridge receiver is inserted into the housing in FIGS. 1-10 for the unified identification. That is, the position of the front panel of the housing is referred as "front", and the position of the back panel of the housing opposite thereto is referred as "back". Specifically, the coordinate system in FIG. 10 is that the direction indicated by the X-axis is referred as "front", the direction indicated by the Y-axis is referred as "right", and the direction indicated by the Z-axis is referred as "upper".

The clamping unit 22 includes a clip-lock assembly 221 and a button assembly 222. The clip-lock assembly 221 includes clip-lock panel 2211 disposed horizontally and an elastic assembly 2212 disposed under the clip-lock panel 2211. An upper panel of the clip-lock panel 2211 is provided with a plurality of cylindrical protrusions 24 whose axes are inclined rearward, and a corresponding lower panel of the cartridge receiver 1 is provided with a plurality of cylindrical slots 13 having the same shape as the cylindrical protrusions 24. Interiors of the cylindrical protrusions 24 and cylindrical slots 13 are respectively provided with male and female electrical interfaces that can match with each other. The cylindrical protrusions 24 pass upward through the clamping port 212 and snap into the cylindrical slots 13 under an action of the elastic assembly 2212, so as to power the laser element and assist in adjusting parameters of the laser element. Preferably, the electrical interfaces of cylindrical protrusions 24 are connected with a power supply and/or a parameter control device for adjusting the laser element through the electrical output joint 29 arranged on the housing 2. Electrical interfaces of the cylindrical slots 13 are respectively directly connected to a port of the power supply inside the laser element and/or parameter control interfaces including an interface for adjusting power, an interface for adjusting wavelength, and an interface for adjusting a pulse.

Figure 6:
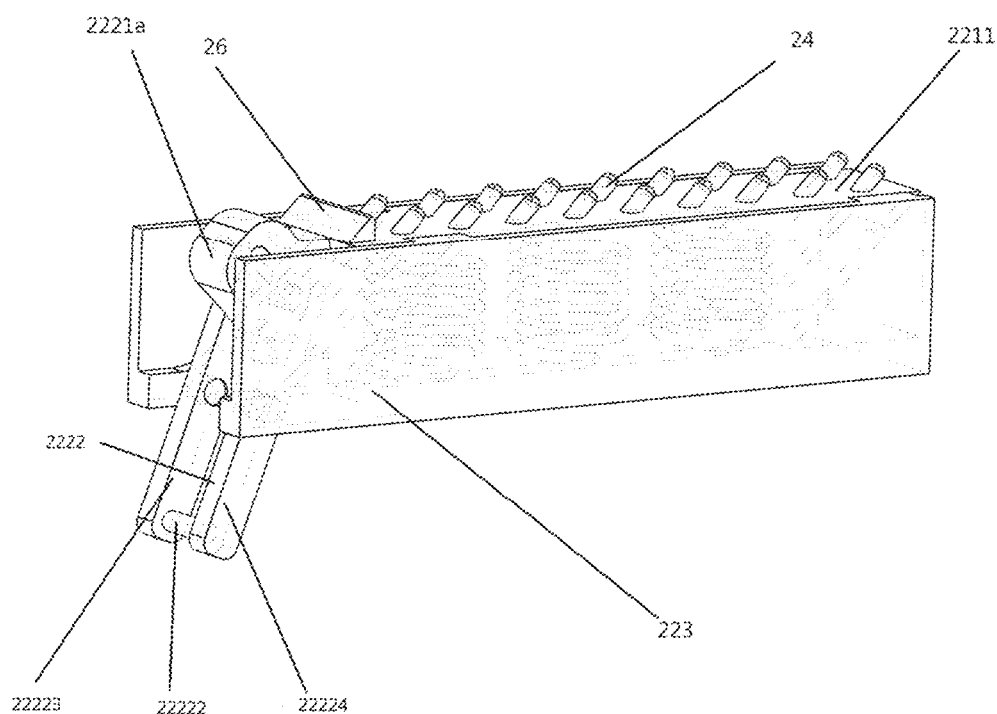
FIG. 6 is a three-dimensional schematic diagram illustrating the structure of the clamping unit of the exchangeable laser according to example 2 of the disclosure.
Figure 7:
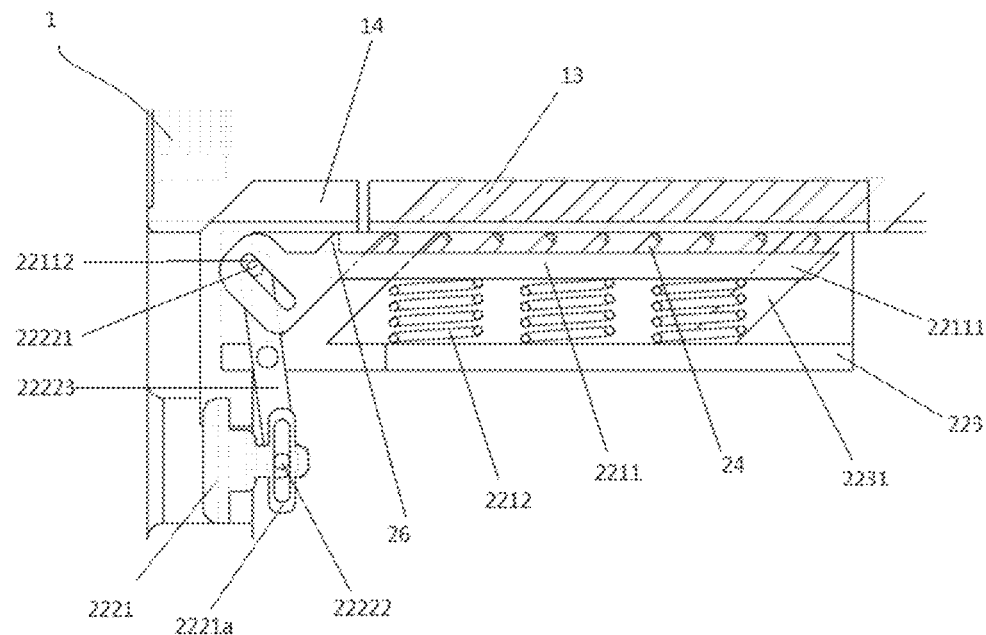
FIG. 7 is a schematic diagram illustrating the structure of the exchangeable laser according to example 2 of the disclosure, in which the clamping unit is not clamped to the cartridge receiver.
Figure 8:
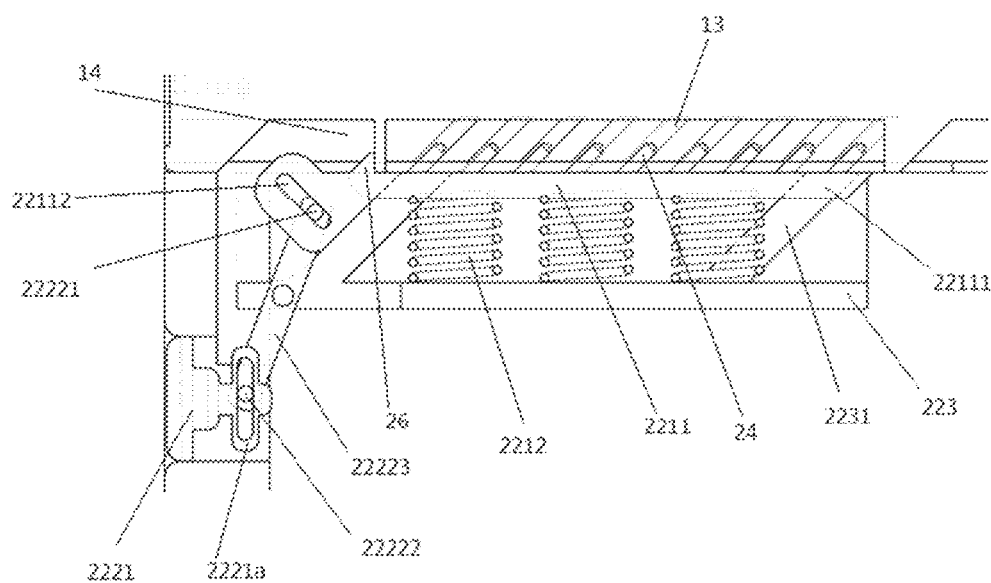
FIG. 8 is a schematic diagram illustrating the structure of the exchangeable laser according to example 2 of the disclosure, in which the clamping unit is clamped to the cartridge receiver.

Specifically, as shown in FIGS. 6-8, when the button assembly 222 moves backward, the clip-lock panel 2211 is driven to move obliquely downward along an axial direction of the cylindrical protrusion 24, the elastic assembly 2212 is switched from a natural state to an energy storage state, and the cylindrical protrusions disengage from the cylindrical slots 13, thereby causing the cartridge receiver 1 to be disengaged from the clip-lock panel 2211. This facilitates the withdrawal of the cartridge receiver 1 from the insertion port 211 and the arrangement of other cartridge receiver having the same structure but including a different laser element that emits laser of different wavelength. That is, the switching of the wavelength of the laser can be completed by simply switching the cartridge receiver 1. When the other cartridge receiver is arranged into the first accommodating space 21 and the button assembly 222 is released (the button assembly 222 is reset forward), the elastic assembly 2212 is switched from the energy storage state to an energy release state, and the clip-lock panel 2211 is moved obliquely upward along the axial direction of the cylindrical protrusions 24 under the action of the elastic assembly 2212, until the cylindrical protrusions 24 engage with the cylindrical slots 13, thereby powering the laser element and/or performing the adjustment of laser elements parameters.

The exchangeable laser of the disclosure is composed of the cartridge receivers 1 and the housing 2 for clamping the cartridge receiver 1, and the cartridge receivers 1 all have a uniform-shaped electrical interface 11 and the optical interfaces 12 and include a laser element inside. The laser element inside each of the cartridge receivers 1 may be composed of a semiconductor laser, a solid laser, a gas laser or other kinds of laser elements. Laser is output through the same optical joint 25 provided at the back of the housing 2. The power supply and parameter control of the laser element are realized by the electronic interfaces of the cylindrical protrusions 24 with the inclined angles of clip-lock panel and cylindrical slots 13 of the cartridge receiver 1. In addition, the cylindrical protrusions 24 with the inclined angles and cylindrical slots 13 with the inclined angles can realize the precise positioning of the housing 2 and the cartridge receiver 1. When replacing by a laser element that emits laser with different wavelength, it is only necessary to withdraw the cartridge receiver 1 from the housing 2, and replace it with another cartridge receiver 1 that includes laser element emitting laser with different wavelength. Therefore, the replacement of the laser elements is converted to the replacement of cartridge receivers that include a different laser element emitting laser with different wavelength, and have consistent shapes, consistent electrical interfaces and optical interfaces, which greatly reduces the difficulty for medical personnel to switch laser wavelengths, and improves the popularization of laser therapeutic instruments in the medical field.

Example 2

Preferably, this example differs from the above example in that: in order to achieve accurate connection of the optical interfaces and the electrical interfaces between the cartridge receiver 1 and the housing 2, the clamping unit 22, as shown in FIGS. 6-8, further includes a clamping box 223. The clamping box 223 is fixed to the second accommodating space 23. In addition, a lower portion of the elastic assembly 2212 is fixed to a bottom of the clamping box 223. When the clip-lock panel 2211 is moved up and down, the clip-lock panel is not completely detached from the clamping box 223. A left and right sides of the clamping box 223 are respectively provided with a plurality of inclined guide rails 2231 having the same inclination degree as the axis of the cylindrical protrusion 24, and a left and right sides of the clip-lock panel 2211 corresponding to the clamping box are provided with inclined guide channels 22111 respectively. Alternatively, the left and right side surfaces of the second accommodating space 23 are preferably provided with a plurality of inclined guide rails having the same inclination degree as the axis of the cylindrical protrusion 24, and the left and right sides of the clip-lock panel 2211 corresponding to the second accommodating space are provided with inclined guide channels. In addition, the lower portion of the elastic assembly 2212 is fixed to a bottom of the second accommodating space 23. When the clip-lock panel 2211 is moved up and down, the clip-lock panel is not completely detached from the inclined guide rails.

Preferably, as shown in FIGS. 6-8, the button assembly 222 includes a release button 2221 arranged at the front panel of the housing 2 corresponding to the second accommodating space 23, and a frame connector 2222 arranged behind the release button 2221. A vertical strip-shaped slot 2221*a* is provided backside of the release button 2221, and an inclined strip-shaped slot 22112 is provided frontside of the clip-lock panel 2211. The vertical strip-shaped slot 2221*a* and the inclined strip-shaped slot 22112 have openings oriented perpendicular to left and right panels of the housing 2, respectively. An inclined direction of the inclined strip-shaped slot 22112 is perpendicular to the axis of the cylindrical protrusion 24. An upper rod 22221 and lower rod 22222 of the frame connector 2222 are respectively capable of sliding in the inclined strip-shaped slot 22112 and the vertical strip-shaped slot 2221*a*. A left rod 22223 and right rod 22224 of the frame connector 2222 are horizontally hinged to the left and right panels of the clamping box 223, respectively. When the release button 2221 moves backward, the vertical strip-shaped slot 2221*a* moves backward, which allows the lower rod 22222 of the frame connector 2222 rotating obliquely backward in the vertical strip-shaped slot 2221*a*, and in turn allows the upper rod 22221 of the frame connector 2222 rotating obliquely forward in the inclined strip-shaped slot 22112. At the same time, a force direction of the inclined strip-shaped slot 22112 is always the same as an inclination direction of the cylindrical protrusion 24, which allows the clip-lock panel 2211 to move downward along the inclination direction of the cylindrical projection 24.

Preferably, the clamping unit 22 further includes a buckle 26 disposed on the upper portion of the clip-lock panel 2211 and located in front of the cylindrical protrusion 24, and a buckle slot 14 is provided under the corresponding lower panel of the cartridge receiver 1 at a position corresponding to a position of the buckle. When the back panel of the cartridge receiver 1 is connected with the back panel of the housing 2, the buckle 26 exactly snaps into the buckle slot 14, and the male and female electrical interfaces inside the cylindrical protrusion 24 and the cylindrical slots 13 corresponding to the cylindrical protrusion are connected with each other, preventing the cartridge receiver 1 from slipping out of the housing 2 during use.

Preferably, an upper back portion of the cartridge receiver 1 is further provided with a heat sink 15 of the laser element. Preferably, a middle portion of the heat sink 15 is provided with a cooling inlet 151 for heat sink penetrating vertically, and the upper panel of the housing 2 is provided with a forced air cooling inlet 27 at a position corresponding to a position of the cooling inlet 151 for heat sink. The left panel and/or the right panel of the housing 2 are arranged with forced air cooling outlets 28, respectively, as shown in FIGS. 1-5. The heat sink 15 has a sheet-like multi-layer structure. An external active air-cooling device enters the air through the forced air cooling inlet 27, allowing the air to flow vertically and horizontally to the forced air cooling outlet 28 to perform forced wind cooling of the heat sink 15.

The front panel of the cartridge receiver 1 is provided with a display device or a warning light 18 to prompt completion of the connection after the laser element is ready for connection and to prompt that the laser is being outputted when the laser element is working.

Preferably, the optical interface 12 has a concave tapered cavity for cooperating with the laser outlet of the laser element, and outputs laser through an optical fiber ferrule. One end of the electrical interface 11 is connected to the electrical interface of the laser element, and the other end is connected to the uniform electrical input joint 29 of the housing.

Preferably, the cylindrical protrusions 24 are arrayed on the upper surface of the clip-lock panel 2211, and the cylindrical slots 13 are arrayed on the lower panel of the cartridge receiver 1, corresponding to the array of the cylindrical protrusions. Specifically, as shown in FIGS. 6-8, 18 cylindrical slots 13 are arrayed on the lower panel of the cartridge receiver 1 in two rows at an angle of 45° with the horizontal plane. Each of the cylindrical slots 13 is provided with an annular barrel-shaped metal ferrule, and the center of the metal ferrule has a cavity structure. In this example, the cavity has a diameter of 3 mm and a length of 5 mm, allowing the insertion of needle-like pins inside the cylindrical protrusion 24. Correspondingly, 18 cylindrical protrusions 24 are arrayed on the upper panel of the clip-lock panel in two rows at an angle of 45° with the horizontal plane. The cylindrical protrusions 24 are internally provided with electrical pins for matching the internal structure of the cylindrical slots 13. After the cartridge receiver 1 is inserted into the first accommodating space 21 of the housing 2, the cartridge receiver 1 is locked by the clamping unit 22; and when the lock state is released by pressing the release button 2221, the cartridge receiver 1 can be taken out from the first accommodating space 21.

When the cartridge receiver 1 is not inserted into the housing 2, the clip-lock panel 2211 and the cylindrical projections 24 are lifted under the action of the spring assembly 2212. As shown in FIG. 7, the back panel of the clip-lock panel 2211 is inclined, and the inclined back panel always has a portion in contact with an inclined side of the clamping box 223. The inclined surface has the same inclination angle as that of the axis of the cylindrical protrusion 24. When the cartridge receiver 1 is inserted, the release button 2221 is pressed, and the inclined panel of clip-lock panel 2211 is forced to move downward, while the cylindrical protrusion 24 and the electrical ferrule inside thereof are moved downward, so that the cartridge receiver 1 can be inserted. After the cartridge receiver is inserted to reach a certain depth, for example, the back panel of the cartridge receiver 1 abuts against to the back panel of the housing 2 or the back panel of the cartridge receiver 1 abuts against the positioning block disposed on the back panel of the housing 2, as shown in FIG. 8, the release button 2221 is released, the clip-lock panel 2211 is bounced, and the cylindrical protrusion 24 and the electrical ferrule inside thereof are inserted into the cylindrical slots 13 and the electrical ferrule, to realize the communication of the circuit. At the same time, the optical interfaces 12 are cooperated to achieve optical communication. Under the action of the elastic assembly 2212, such as a spring, the cartridge receiver 1 is subjected to a rearward force to press the electrical interface 11 and optical interfaces 12. In addition, under the restriction of the buckle 26, the cartridge receiver 1 cannot be loosened or accidentally taken out.

Example 3

Preferably, a back panel of the housing 2 is provided with an optical joint 25 at a position of the back panel horizontally corresponding to the insertion port 211, and the cartridge receiver 1 is provided with an optical interface 12 for matching the optical joint at a position corresponding to the optical joint. The optical interface 12 is internally connected to a laser output port of the cartridge receiver via optical fibers. Different cartridge receivers are designed to have uniform optical interfaces 12 and electrical interface 11, which greatly reduces the difficulty for medical personnel to switch laser wavelengths, and improves the popularization of laser therapeutic instruments in the medical field.

Figure 9:
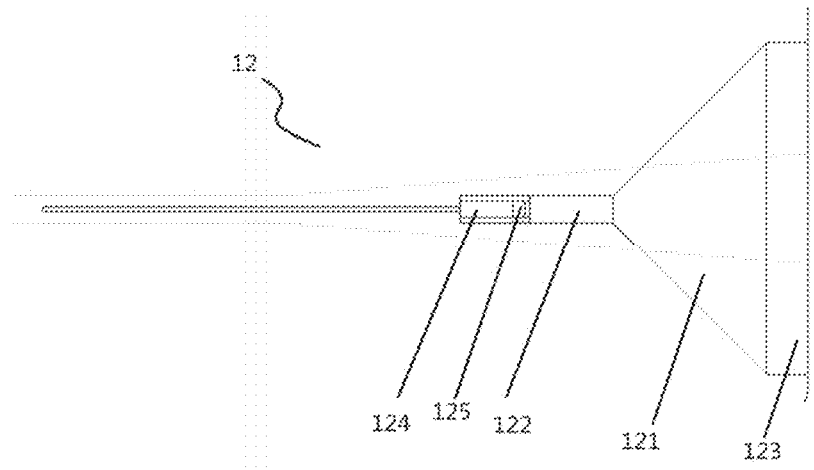
FIG. 9 is a schematic diagram illustrating an optical interface of the exchangeable laser according to example 3 of the disclosure.
Figure 10:
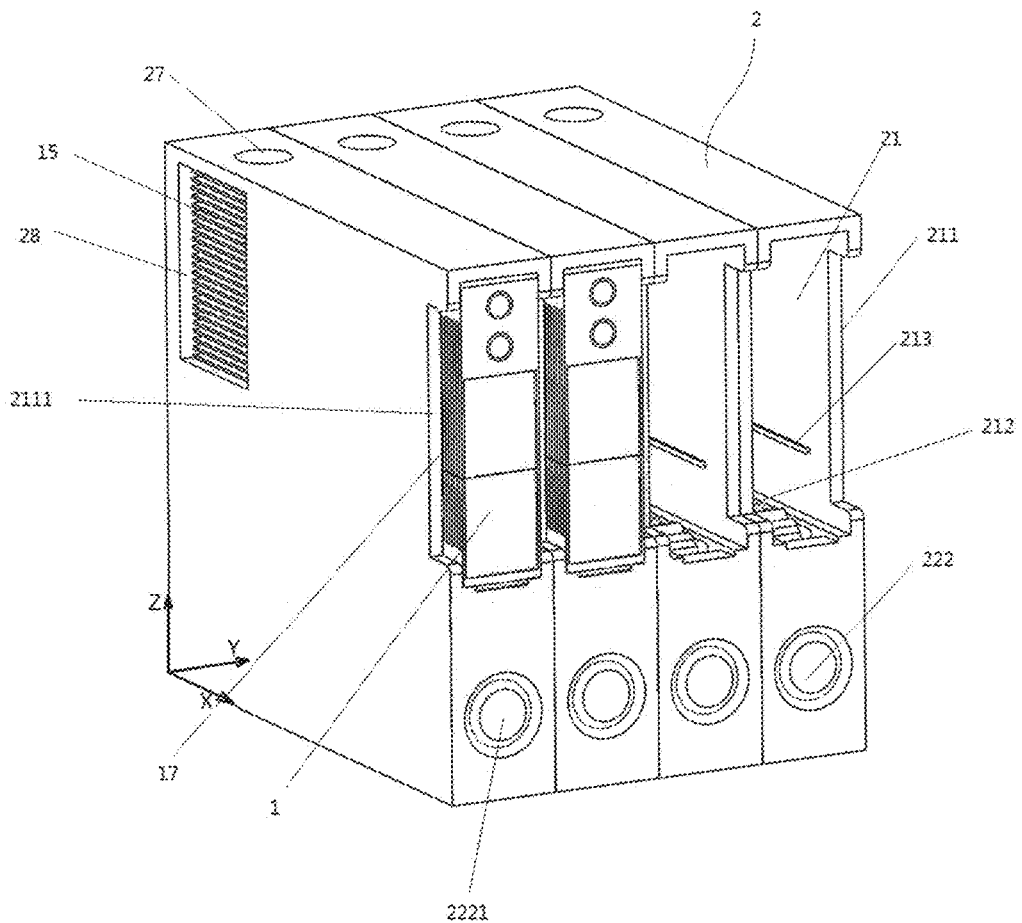
FIG. 10 is a three-dimensional schematic diagram illustrating the structure of the exchangeable laser array according to example 4 of the disclosure.
Figure 11:
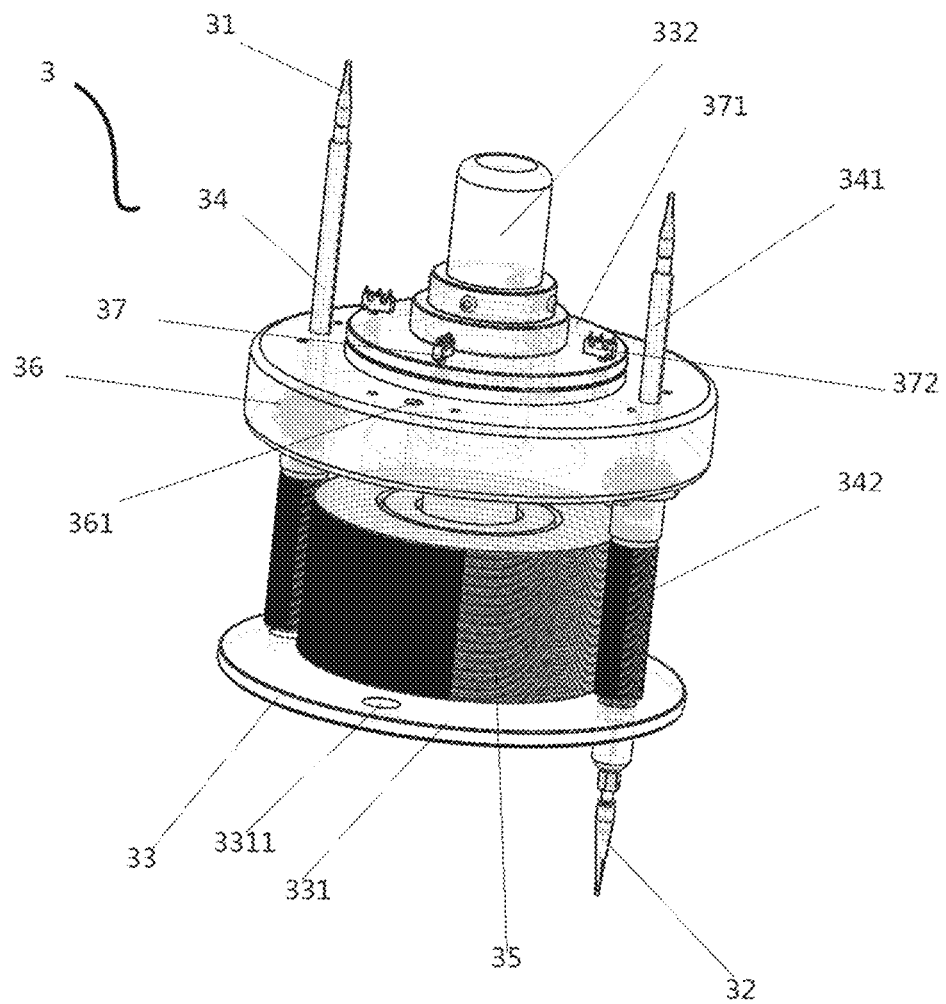
FIG. 11 is a three-dimensional schematic diagram illustrating the structure of the wavelength switcher of the exchangeable laser according to example 5 of the disclosure.
Figure 12:
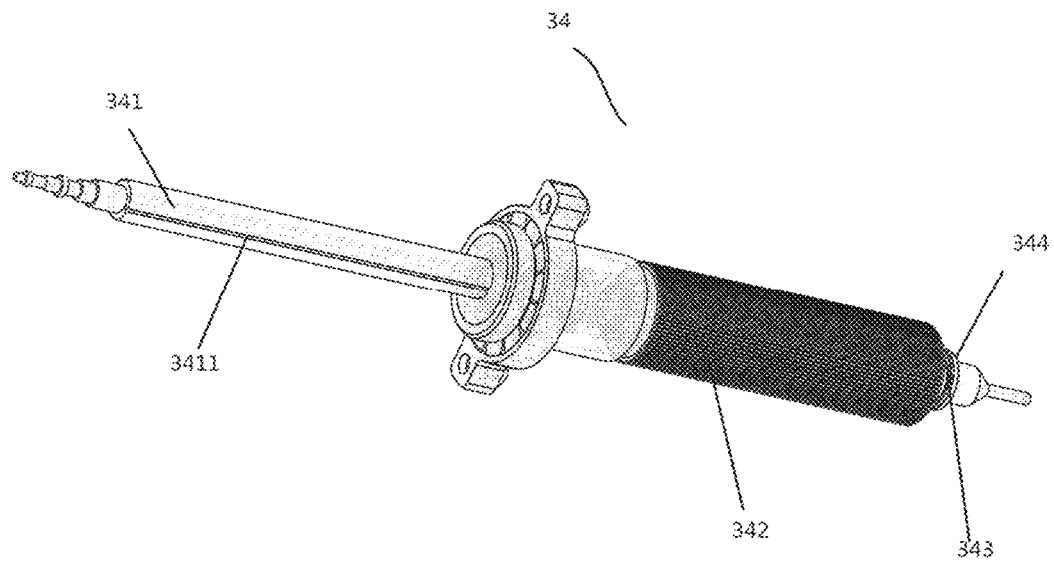
FIG. 12 is a three-dimensional schematic diagram illustrating the structure of the optical fiber plug of the exchangeable laser according to example 5 of the disclosure.
Figure 13:
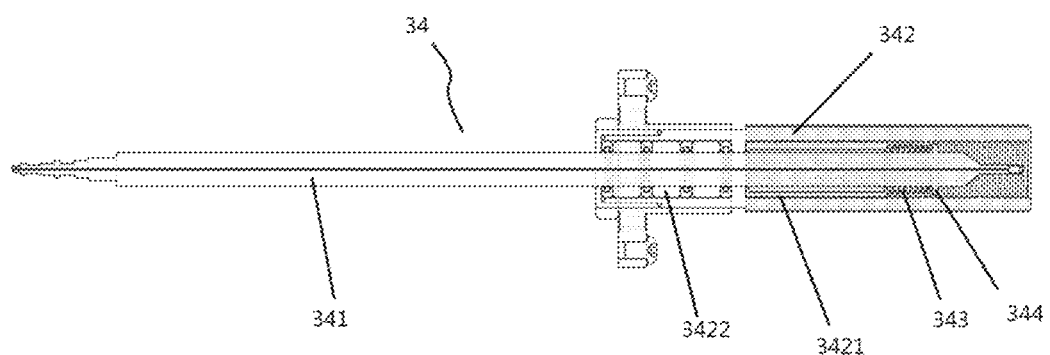
FIG. 13 is a cross-sectional schematic diagram illustrating the structure of the optical fiber plug of the exchangeable laser according to example 5 of the disclosure, in which the optical fiber plugging rod is located at an extreme position.
Figure 14:
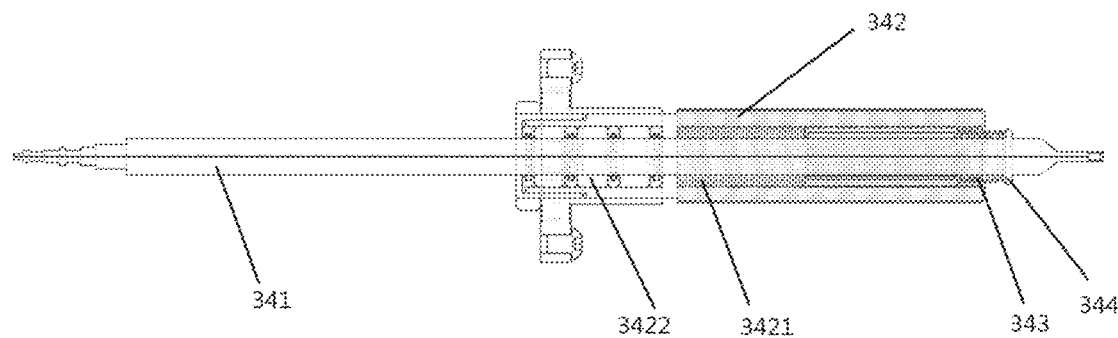
FIG. 14 is a cross-sectional schematic diagram illustrating the structure of the optical fiber plug of the exchangeable laser according to example 5 of the disclosure, in which the optical fiber plugging rod is located at a plugging position.
Figure 15:
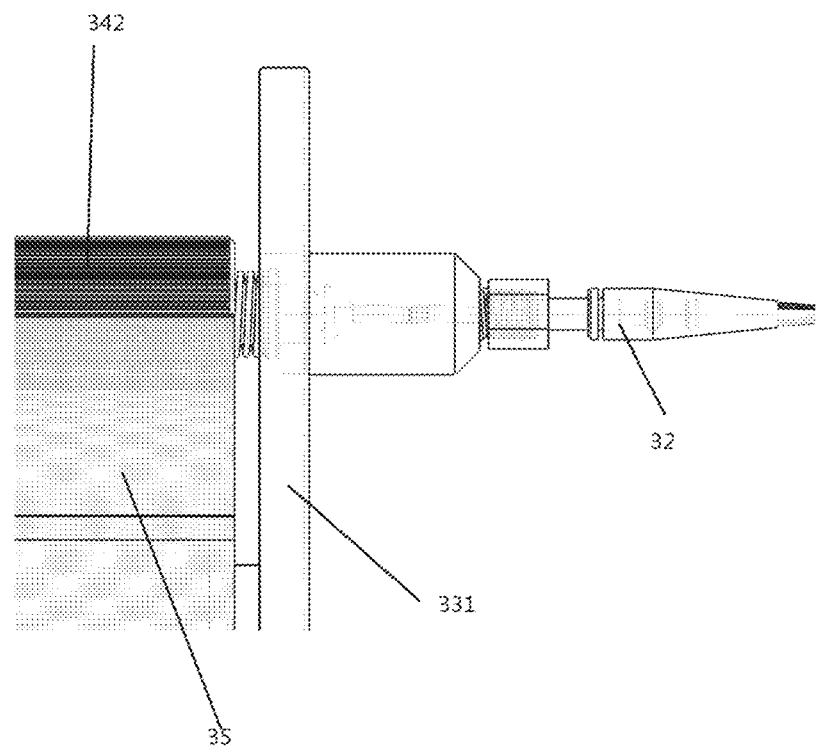
FIG. 15 is a partial diagram illustrating the structure that the optical fiber plugging rod is inserted into the optical fiber output interface, according to the exchangeable laser of example 5 of the disclosure.

In particular, as shown in FIG. 9, the optical interface 12 of the cartridge receiver 1 includes a tapered cavity 121 with a cone top at front and an axis extending rearward. A small cylindrical cavity 122 is arranged extending horizontally forward from the cone top of the tapered cavity 121 and is communication with the tapered cavity. A big cylindrical cavity 123 is arranged extending horizontally backward from a cone bottom of the tapered cavity 121. A front side of the small cylindrical cavity 122 is directly connected a laser output port of the laser element, or connected to the laser output port of the laser element through an optical fiber ferrule 124.

Figure 2:
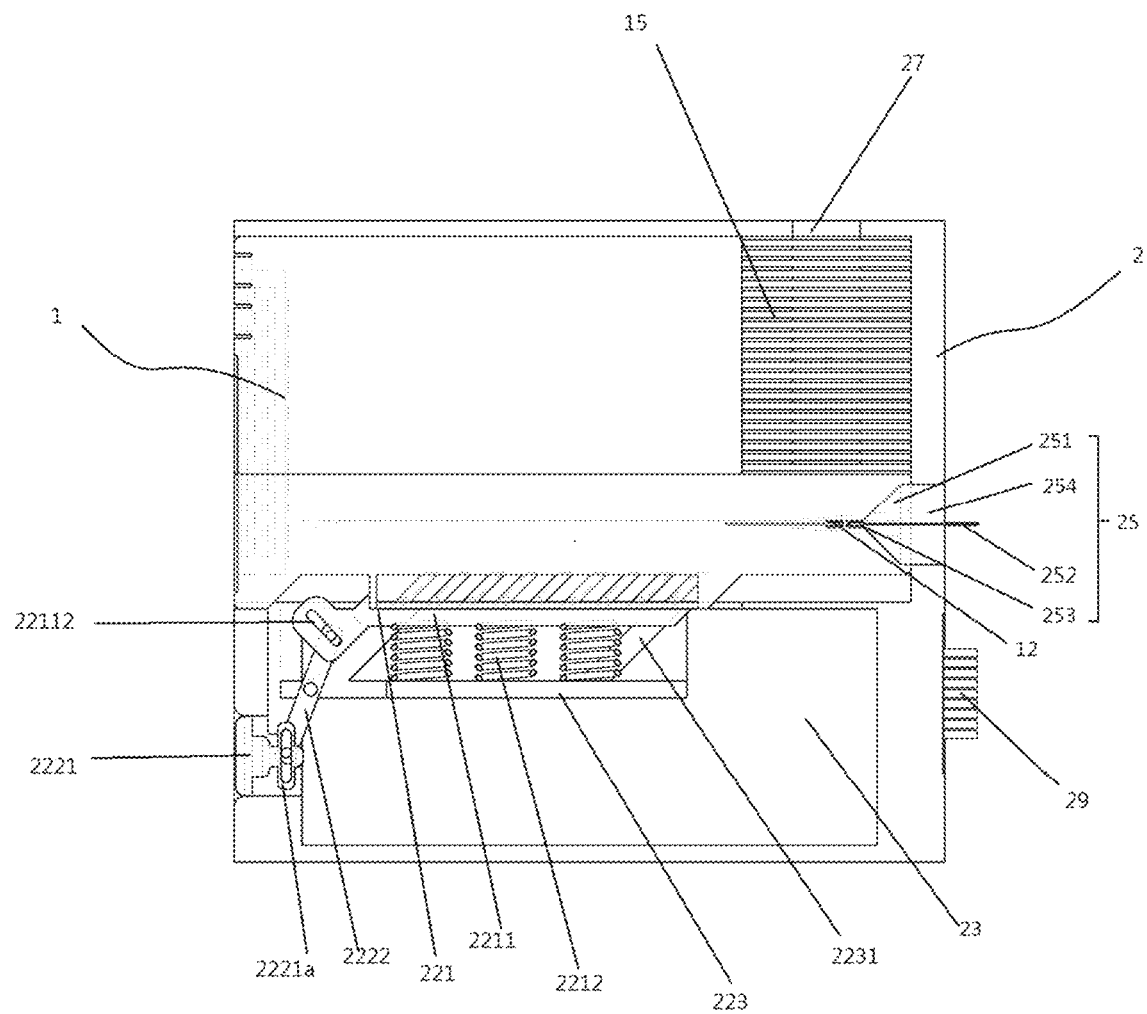
FIG. 2 is a cross-sectional schematic diagram from the right view illustrating the structure of the exchangeable laser according to example 1 of the disclosure.

The back panel of the housing 2 is provided with an optical joint 25 (i.e., an optical connector) capable of matching with the optical interface of the cartridge receiver. As shown in FIG. 2, the optical joint 25 includes a tapered adapter 251 having the same shape as the tapered cavity 121, and an external optical fiber 252 disposed inside the tapered adapter 251. A front end of the external optical fiber 252 is provided with an external optical fiber ferrule 253 capable of inserting into the small cylindrical cavity 122. The external optical fiber ferrule 253 is arranged at a front end of the tapered adapter 251, and a cylindrical adapter 254 with the same shape as the large cylindrical cavity 123 is arranged extending forwardly from a back end of the tapered adapter 251. The cylindrical adapter 254 may extend to be flush with the back panel of the housing 2.

A top portion of the optical fiber ferrule 124 has a lens 125, and the lens is a convex lens or a lenticular lens or a graded-index lens. When the optical interface 12 is mated with the optical joint 25, a distance between a front end face of an optical fiber of the external optical fiber ferrule 253 and the lens is equal to a focal length of the lens, or half of it or an integral multiple thereof, collimating the divergent light emitting from the optical fiber. In this example, a core diameter of the optical fiber is 400 μm, and the optical fiber ferrule 124 has a diameter of 3 mm, and the lens is a convex lens 125. The small cylindrical cavity 122 allows the insertion of the external optical fiber ferrule 253.

The optical fiber ferrule 124 of the laser element outputs laser in a collimated manner, and is coupled with the external optical fiber ferrule 253 inside the housing 2, so as to output laser through the external optical fiber 252. There is a gap between the top end of the optical fiber ferrule 124 of the laser element and the top end of the external optical fiber ferrule 253 of the housing 2, preventing the top end of the optical fiber ferrule 124 and the top end of the external optical fiber ferrule 253 from being damaged by the external force collision. The gap may be in a size of 10 μm-1000 μm. In this embodiment, this gap is 500 μm.

Preferably, the tapered cavity has a taper angle of 45°. The arrangement of the tapered adapter 251 and the tapered cavity 121 having the taper angle of 45° as well as the mechanical structures of the large cylindrical cavity 123 and the cylindrical adapter 254, enable the optical fiber ferrule 124 of the laser element and the external optical fiber ferrule 253 can be precisely docked with each other.

Figure 3:
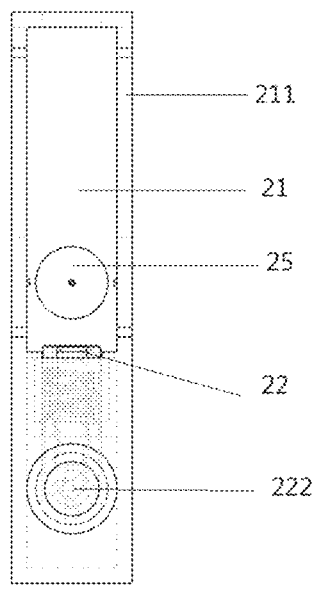
FIG. 3 is a schematic diagram from the front view illustrating the structure of the structure of the exchangeable laser according to example 1 of the disclosure.
Figure 4:
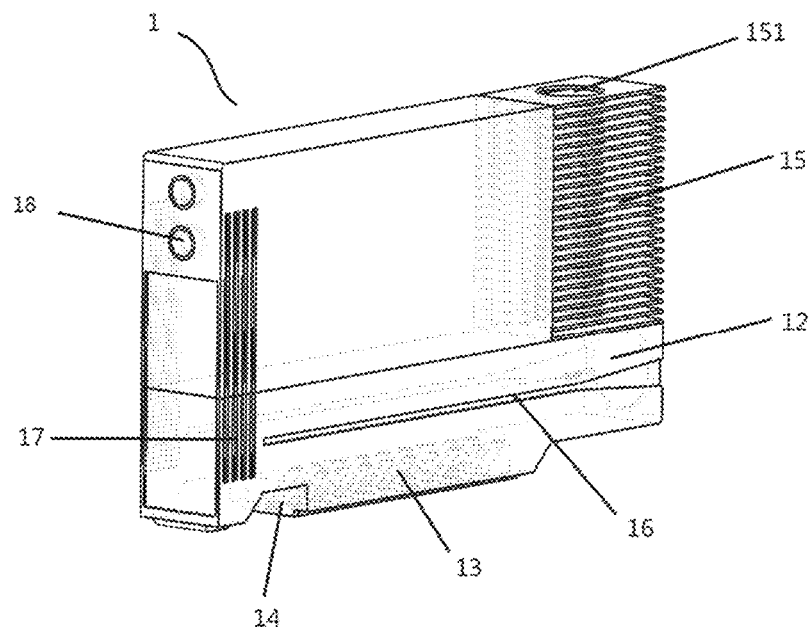
FIG. 4 is a three-dimensional schematic diagram illustrating the structure of the cartridge receiver of the exchangeable laser according to example 1 of the disclosure.
Figure 5:
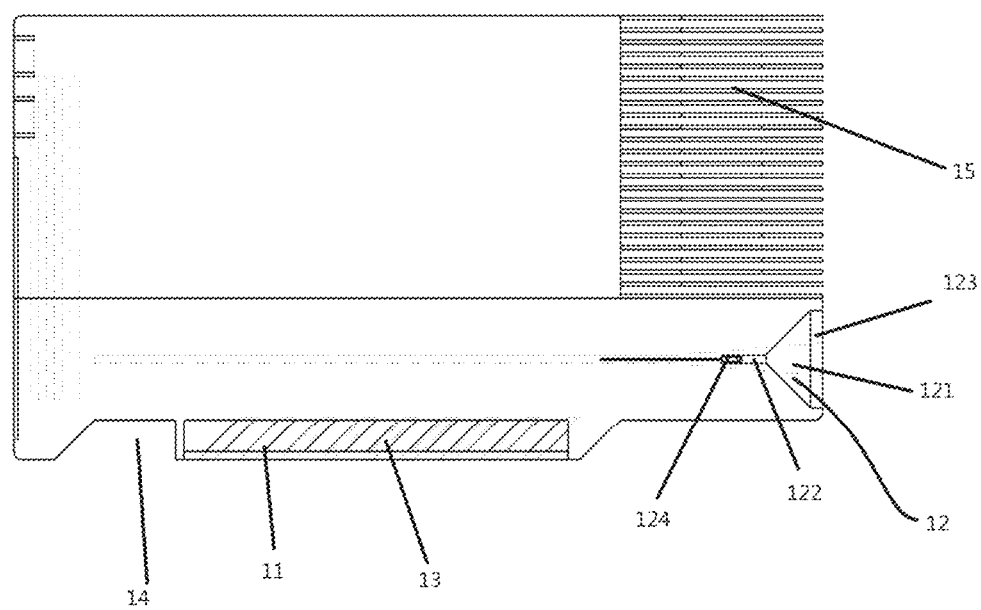
FIG. 5 is a cross-sectional schematic diagram from the right view illustrating the structure of the cartridge receiver of the exchangeable laser according to example 1 of the disclosure.

FIGS. 1-3 show the structure of the cartridge receiver when it is not inserted into the housing 2. Preferably, the first accommodating space 21 and the cartridge receiver 1 have a same shape. The left panel and the right panel of the cartridge receiver 1 are provided with horizontal positioning grooves 16, and the left panel and the right panel of the first accommodating space 21 corresponding to the left panel and the right panel of the cartridge receiver 1 are provided with horizontal positioning protrusions 213.

Preferably, a front portion of the left panel and the right panel of the cartridge receiver 1 is provided with an anti-slip groove structure 17, and the plugging port 211 further includes plugging cartridge receiver grooves 2111 for the cartridge receiver corresponding to the anti-slip groove structure 17 in front of the left panels and right panel of the housing 2. This is convenient for the use to remove the cartridge receiver 1 from the housing 2 by hand.

Example 4

An exchangeable laser array is provided. The exchangeable laser array includes at least two of the above-mentioned exchangeable lasers, and in each of exchangeable laser, a left side and right side of the housing are respectively provided with a horizontal guide channel array and a horizontal guide rail array. A plurality of exchangeable lasers can be snap-fitted side-by-side through the horizontal guide channel array and horizontal guide rail array, and it is easy to disassemble and replace the exchangeable lasers. In addition, as a preferred solution, the housing 2 also has a forced air cooling outlet 28 at a position corresponding to the back panel of the heat sink.

The exchangeable laser array is composed of the plurality of exchangeable lasers that have the same shape and the same output interfaces and the housings 2 with the same optical fiber joints 25 and electronic joints. The optical fiber joints 25 of the housings 2 are directly or indirectly connected to external optical fibers, output lasers having multiple wavelengths through different optical fibers to different instruments such as photodynamic therapy devices or dedicated wavelength switchers 3. In particular, as shown in FIG. 10, there are 4 housings 2, and 2 cartridge receivers 1. According to the above manner, the exchangeable laser array of the disclosure can realize the quick and convenient disassembly and assembly of the cartridge receiver 1 (i.e., the laser element). The replacement of the laser element can achieve the switch of different output wavelengths. For example, if there is only a laser element with two emission wavelengths of 630 nm and 664 nm in the cartridge receiver, while Foscan photosensitizer is temporarily used for treatment (the treatment wavelength is 652 nm) during the treatment, then it will be only required to purchase a cartridge receiver with 652 nm emission wavelength, and insert it into a housing in vacant.

The electrical interface of each exchangeable laser of the exchangeable laser array can be connected to the power and control system of the photodynamic therapy device, and thus is powered and controlled by the photodynamic therapy device. The optical fiber output interface of the exchangeable laser array is connected to an external optical fiber. In this example, the array including four housings is connected with four external optical fibers. These external optical fibers can be directly connected with wavelength switchers to realize wavelength selection output, or respectively connected with different photodynamic therapy devices.

Wavelength switchers can be implemented in a variety of ways. For example, the output wavelength can be selected by coupling an all-in-one optical fiber coupler to one output optical fiber and controlling the output wavelength of the laser array, or multiple wavelengths can be multiplexed and selected through a wavelength division multiplexer (WDM). In addition, the coupling and switching of the plurality of optical fibers to one or more optical fibers can be controlled by mechanical motion.

Example 5

Figure 18:
FIG. 18 is a schematic diagram illustrating the mechanical coupling and switching principle in optical fibers between the exchangeable laser according to example 5 of the disclosure and the wavelength switcher.

FIG. 18 shows the principle of mechanical coupling and switching of optical fibers between the exchangeable laser and the wavelength switcher. Through the relative positional change among the plurality of fiber optical plugs that are connected to the plurality of optical fiber input interfaces, and the optical fiber output interface, when a certain input optical fiber is aligned with the optical fiber output interface, laser in the optical fiber connected to this optical fiber plug is output, so as to realize switching of different wavelength outputs.

To ensure the efficiency of optical fiber coupling, it is required the precise alignment effect among the optical fiber plugs and optical fiber output interfaces. In order to achieve this effect, it is necessary to optimize the simple displacement motion into a cyclic motion of displacement-insertion-extraction-displacement, or to simulate the action of manually inserting an optical fiber interface by mechanical automatic motion. In order to achieve the above complex motions, the present disclosure adopts the following scheme.

The wavelength switcher 3, as shown in FIGS. 11-19, includes a plurality of optical fiber input interfaces 31 connected (directly or indirectly) to optical joints 25 of exchangeable lasers of the exchangeable laser array, the fiber output interface 32, a base 33 and a plurality of optical fiber plugs 34. The base 33 includes a baseplate 331 and a stationary shaft 332 extending upward along a center of the baseplate 331. The stationary shaft 332 is fixed with a drive gear 35 and an optical fiber displacement disk 36 that coincide with an axis of the stationary shaft 332 from bottom to top. The base 33 is not rotatable and movable, and is a center where the wavelength switcher 3 is fixed to the other peripheral devices. Preferably, a bearing is provided between the drive gear 35 and/or the fiber displacement disk 36 and the stationary shaft 332.

The optical fiber plugs 34 include optical fiber plugging rods 341, a driven gear 342 disposed at a periphery of the optical fiber plugging rods 341 and meshing with the drive gear 35. The optical fiber insertion rod 342 is provided with an optical fiber at an axial position thereof. One end of the optical fiber plugging rod 342 is connected to the optical fiber input interface 31, and other end of the optical fiber plugging rod is connected to the optical fiber output interface 32; and vice versa.

Preferably, the optical fiber plugs 34 are uniformly or axisymmetrically disposed on the optical fiber displacement disk 36 at a radial periphery of the drive gear 35. Several output ports 3311 for spirally connecting the optical fiber output interfaces 32 are disposed on the baseplate 331 vertically corresponding to the optical fiber plugs 34. The optical fiber output interface 32 is provided with an external thread for spirally connecting the output ports 3311, adaptively.

Several optical fiber plugging ports 361 for positioning the optical fiber plugs 34 are disposed on the optical fiber displacement disk 36 at a radial periphery of the drive gear 35.

When the optical fiber plugging rods 341 are located above the baseplate 331, the optical fiber displacement disk 36 is rotated under an action of the drive gear 35 and driven gear 342, and thus the optical fiber plugs 34 are rotated about the axis of the stationary shaft 332; when the optical fiber plugging rods 341 are rotated about the axis of the stationary shaft 332 and are rotated above the output ports 3311, the optical fiber plugging rods 341 are moved up or down along the optical fiber plugging ports 361 under the action of the drive gear 35 and driven gear 342, so as to pull out from the output ports 3311 or insert into the optical fiber output interfaces 32.

A large drive gear 35 and a small driven gear 342 are used to form a main transmission structure, and the optical fiber plugs 34 are disposed at a center of the small driven gear 342. When the central shaft of the driven gear 342 is unmovable, the rotation of the drive gear 35 drives the driven gear 342 to rotate, and the rotation of driven gear 342 drives the optical fiber insertion rod 341 to move up and down, thereby completing a insertion-extraction operation of the optical fiber insertion rod 341. When the central shaft of the driven gear 342 is movable, i.e., when the optical fiber plugging rod 341 is completely above the baseplate 331, the driven gear 35 is locked with the optical fiber plug 34 and thus they both cannot be rotated about their own axis, the driven gear 342 drives the fiber displacement plate 36 to rotate along the drive gear 35 under the action of the drive gear 35, thereby realizing the rotational translation of the optical fiber plugs 34.

Figure 16:
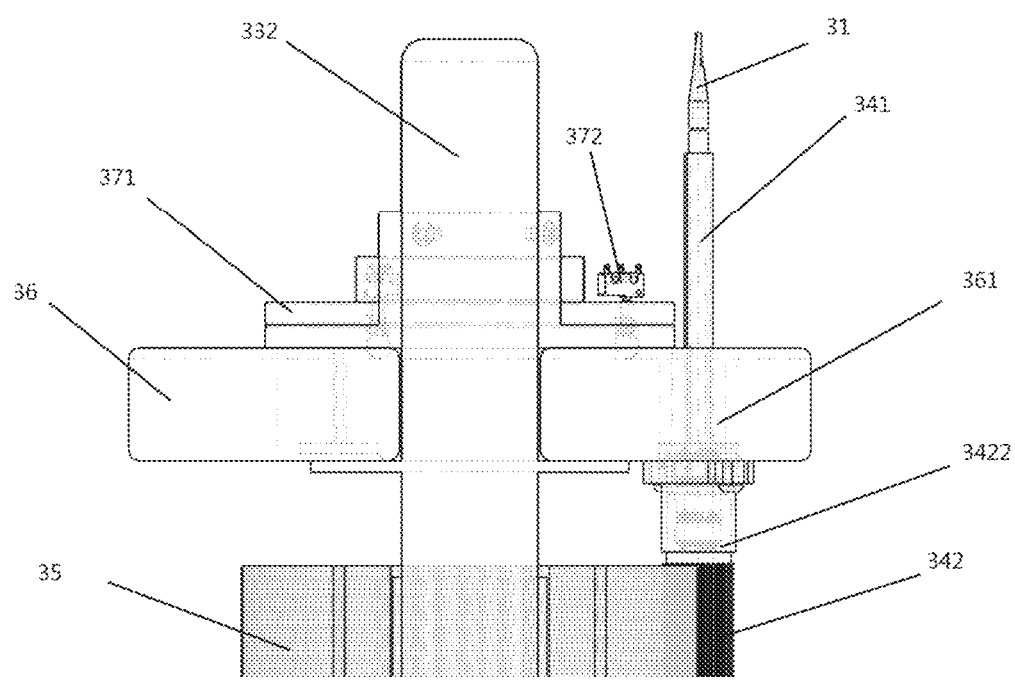
FIG. 16 is a schematic diagram illustrating the structures of the optical fiber displacement disk and micro-switch device of the exchangeable laser according to example 5 of the disclosure.
Figure 17:
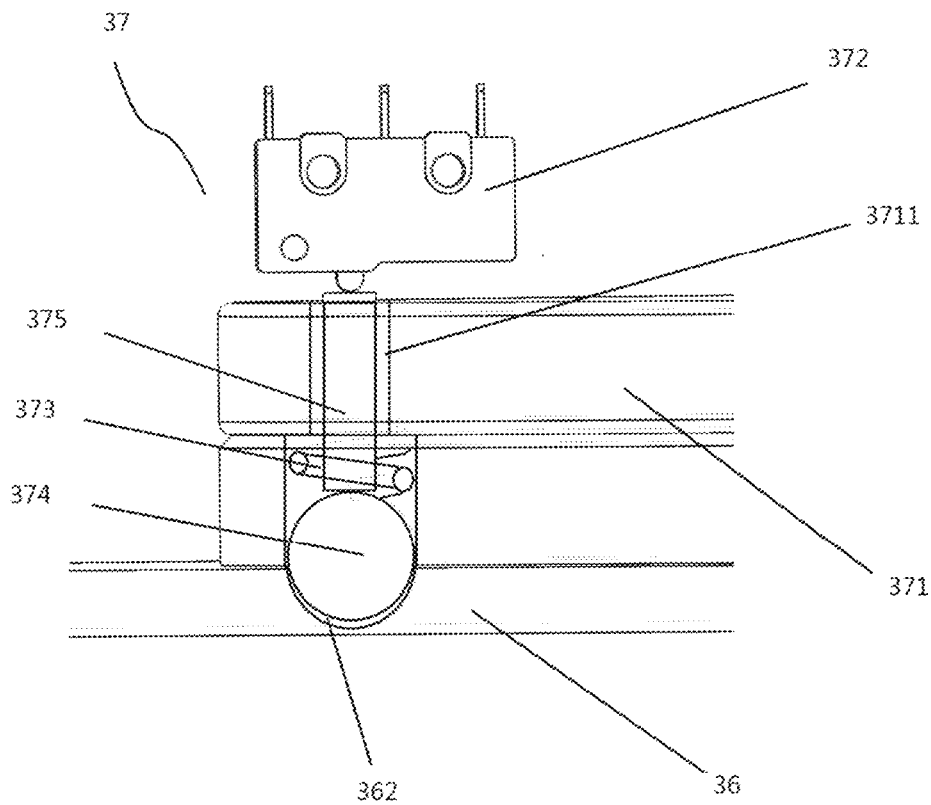
FIG. 17 is a perspective structural diagram of the micro-switch device of the exchangeable laser according to example 5 of the disclosure.

Preferably, as shown in FIGS. 16-17, the wavelength switcher 3 further includes a micro-switch device 37 disposed above the optical fiber displacement disk 36. The micro-switch device 37 includes a micro-switchgear 371, a plurality of micro-switch elements 372, a micro-motion spring 373, a limiting ball 374 and a micro-motion rod 375. The micro-switchgear 371 is provided with micro-slots 3711. The micro-motion spring 373, limiting ball 374 and micro-motion rod 375 are disposed inside the micro-slots 3711. In addition, the micro-motion spring 373 is sleeved on the micro-motion rod 375, and one end of the micro-motion rod 375 abuts against the triggering part of the micro-switch element 372, and the other end abuts against the limiting ball 374. Micro-switch positioning slots 362 with the same angle as the optical fiber plugs 34 are disposed on the optical fiber displacement disk 36. When the optical fiber displacement disk 36 is rotated, the limiting ball 374 is moved from one micro-switch positioning slot 362 to an adjacent micro-switch positioning slots. At the same time, the optical fiber plug 34 is moved from an upper position of one output port 3311 to an upper position of an adjacent output port. Specifically, the optical fiber plugging ports 361 are axisymmetrically disposed on the optical fiber displacement disk 36, and micro-switch positioning slots 362 are adaptively disposed in a radial direction of the optical fiber displacement disk 36 in which the optical fiber plugging ports 361 are located, so as to ensure that the optical fiber plug 34 can be accurately positioned above the output ports 3311 when the optical fiber displacement disk 36 is rotated.

This structure has two main functions: 1. when the optical fiber plug 34 is aligned with the optical fiber output interface 32 of the baseplate 331 and is completely located above the baseplate 331, the limiting ball 374 is rolled into the micro-switch positioning slots of optical fiber displacement disk 36 under the motion of the micro-motion spring 373. After that, the rotation of the optical fiber displacement disk 36 is stopped due to an increase in resistance. The rotation of the drive gear 35 causes the optical fiber plug 34 to rotate along its own axis, and causes the optical fiber plugging rod 341 to move downward until it is inserted into the optical fiber output interface 32 of the baseplate 331. 2. The drive gear 35 is backward rotated, so that the optical fiber plug 34 is driven away from the optical fiber output interface 32 and retracted to the uppermost position. After that, the rotational resistance of the driven gear 342 is increased, and thus the limiting ball 374 is forced to be disengaged from the micro-switch positioning slot 362 on the upper surface of the optical fiber displacement disk 36. Therefore, the optical fiber plug 34 is driven by the drive gear 35 to be displaced to the next optical fiber output interface.

The limiting ball 374 is connected to the triggering unit of the micro-switch elements 372 via the micro-motion rod 375 and the micro-motion spring 373. When the limiting ball 374 is disengaged from the micro-switch positioning slot 362 of the optical fiber displacement disk 36, the position of the limiting ball rises, touching the micro-switch elements 372 to turn the switch on; when the limiting ball 374 enters the micro-switch positioning slot 362 of the optical fiber displacement disk 36, the position of limiting ball drops, and thus the micro switch element 372 will be turned off. According to the signal of the micro-switch elements 372, it can be determined whether or not the limiting ball 374 is in the micro-switch positioning slot 362, so as to control the rotation direction of the drive gear 35.

The wavelength switcher 3 can realize a coupling switching output of wavelength in which the plurality of optical fibers transmitting laser with different wavelength input, but one wavelength outputs by using the drive gear 353. When the input and output fiber interfaces are increased, it is only required to install more optical fiber plugs 34 and coupling optical fiber joints. This avoids the control complexity and the reduction of coupling precision caused by the use of multiple rotation and displacement control devices when the number of fiber interfaces increases. The output of the wavelength switcher 3 described above can be used not only with one output optical fiber, but also with two or more optical fiber outputs, the principle of which is similar to that of one optical fiber.

Preferably, the driven gear 342 is connected to the optical fiber plugging rods 341 through a screw-nut pair 3421. On the optical fiber plugging rods 341, lower portions of the optical fiber plugging rods 341 are provided with vertical positioning slots 3411 matching with positioning protrusions of the optical fiber plugging ports 361. The vertical positioning slots 3411 are locked with the positioning protrusions in the optical fiber plugging ports 361, so that the optical fiber plugging rods 341 do not rotate relative to the optical fiber displacement disk 36. A screw external thread matching with a screw internal thread of the driven gear is provided on the optical fiber plugging rods 341 below the vertical positioning slots 3411. When the driven gear 342 rotates, the optical fiber plugging rods 341 are pushed up and down by the screw-nut pair 3421.

Preferably, an optical fiber plugging rod bearing 3422 is provided between the driven gear 342 and the optical fiber plugging rods 341. The optical fiber plugging rod bearing 3422 is composed of at least two bearings capable of withstanding axial opposite forces. In this example, there are three optical fiber plugging rod bearings 3422, which ensures smooth rotation and smooth movement up and down.

The drive gear 35 may be disposed between, above or below the baseplate 33 and the optical fiber displacement disk 36, and the position thereof may be flexibly adjusted as needed.

Preferably, a lower portion of the screw internal thread is provided with a spring 343 and a spring positioning shoulder 344. Preferably, below the spring positioning shoulder 344 is an optical fiber ferrule connected to the optical fiber output interface 32.

The arrangement of the spring 343 and the spring positioning shoulder 344 enable the optical fiber plugging rod 341 to be elastically inserted into the optical fiber output interface 32, avoiding the damage of head portion of the optical fiber ferrules at the bottom. In addition, there is a downward force after insertion, so that the coupling between the fiber ferrules is tight enough without loosening.

Preferably, the screw internal thread of the driven gear 342 is longer than the screw external thread of the optical fiber plugging rod 341. When a top of the screw external thread abuts against a top of the screw internal thread, and/or when a bottom of the vertical positioning slot 3411 abuts against the bottom of the vertical positioning protrusion of the optical fiber plugging port 361. The bottom of the optical fiber plugging rod 341 is located at least completely above the baseplate 331, so that the optical fiber plugging rod 341 is retracted from the optical fiber output interface 32 under the action of drive gear and driven gear, and is retracted to such as an extreme position shown in FIG. 13. The screw external thread reaches the upper end of the screw internal thread, and/or the positioning protrusion of the optical fiber plugging port 361 reaches the bottom of the vertical positioning slot 3411 on the fiber plugging rod 341, so that the driven gear 342 will not be able to rotate along its own axis—which drives the fiber displacement plate 36 to rotate. The extreme position of the optical fiber plugging rod 341 is defined at where the screw external thread reaches the upper end of the screw internal thread, and/or the positioning protrusion of the optical fiber plugging port 361 reaches the bottom of the vertical positioning slot 3411 on the fiber plugging rod 341. The docking position of the fiber plugging rod 341 and the optical fiber output interface 32 is accurately positioned by the number of turns of the drive gear 35 in the reverse direction.

Figure 19:
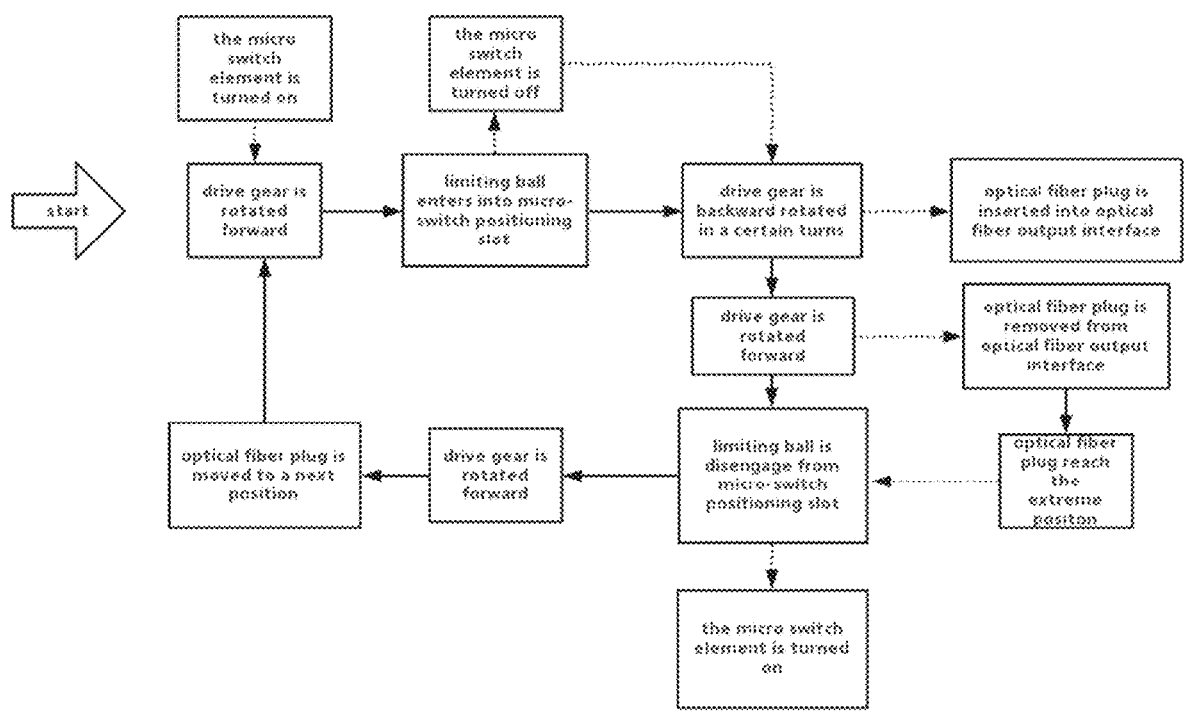
FIG. 19 is a flow chart showing the operation of the wavelength switcher of the exchangeable laser according to example 5 of the disclosure.

The flowchart of the disclosure is shown in FIG. 19.

Before the start state, the optical fiber plugging rod 341 is completely located above the baseplate, and the screw external thread reaches the upper end of the screw internal thread and/or the positioning protrusion of the fiber plugging port 361 reaches the bottom of the vertical positioning slot 3411 on the fiber plugging rod 341. That is, the optical fiber plugging rod 341 is positioned at the extreme position (i.e., the optical fiber plugging rod 341 is pulled out to the extreme position in the upward direction), the limiting ball 374 is located in the micro-switch positioning slot 362.

In the first stage, the rotation of the optical fiber displacement disk 36 drives the optical fiber plug 34 to move from the current optical fiber output interface 32 to the next optical fiber output interface. Specifically, the drive gear 35 is controlled to rotate in the forward direction, which drives the optical fiber displacement disk 36 to rotate, removes the limiting ball 374 from the micro-switch positioning slot 362, and thus turns on the micro-switch element 374. The limiting ball 374 is snapped into the next micro-switch positioning slot of the optical fiber displacement disk 36 under the rotation of the optical fiber displacement disk 36, and the micro-switch element 374 is turned off. The turning on or off of the micro-switch element controls the backward rotation of drive gear 35.

In the second stage, the optical fiber plugging rod 341 of the optical fiber plug 34 is moved downwardly to dock with the optical fiber output interface 32. Specifically, the drive gear 35 is backward rotated, and rotated in a certain turns, which drives the optical fiber plugging rod 341 to move downwardly to the optical fiber output interface 32 and laser-coupled output to the photodynamic therapy device for photodynamic therapy.

In the third stage, the optical fiber plugging rod 341 of the optical fiber plug 34 is moved upwardly to the extreme position. Specifically, when the treatment is completed, the drive gear 35 is controlled to rotate in the forward direction, and the optical fiber plugging rod 341 is moved upwardly and gradually removed from the optical fiber output interface 32, is finally moved to the position before the start state described above, so as to complete a use period.

The control of the forward rotation of the drive gear may be performed by a control system provided in the wavelength switcher 33, or may be performed by the photodynamic therapy device. Specifically, a start switch may be provided on the control system manipulation interface of the wavelength switcher 33 or on the control interface of the photodynamic therapy device. The drive gear is converted from forward rotation to backward rotation during a complete turning on and off of the micro-switch element 37.

It should be noted that the above description is only intended to enable those skilled in the art to more fully understand the present disclosure without limiting the present discourse in any way. It should be appreciated that various modifications and changes can be made to the present disclosure, although the present disclosure has been described above and illustrated in the accompanying drawings. Any modifications, equivalents, improvements, etc. made within the spirit and scope of the present disclosure are intended to be included within the scope of the present disclosure.

The invention claimed is:

1. An exchangeable laser, comprising a cartridge receiver and a housing, wherein a laser element is fixed inside the cartridge receiver, and the housing is used for clamping the cartridge receiver; the cartridge receiver has a unique optical interface and a plurality of electrical interfaces for docking with the housing;

the housing comprises a first accommodating space for accommodating the cartridge receiver, a clamping unit, and a second accommodating space for accommodating the clamping unit;

a front panel of the housing is provided with an insertion port for horizontally inserting the cartridge receiver into the first accommodating space;

the second accommodating space is disposed under the first accommodating space and is communication with the first accommodating space through a clamping port provided on a bottom panel of the first accommodating space;

the clamping unit comprises a clip-lock assembly and a button assembly, the clip-lock assembly comprising a clip-lock panel disposed horizontally and an elastic assembly disposed under the clip-lock panel;

an upper panel of the clip-lock panel is provided with a plurality of cylindrical protrusions with axes inclined rearward, and a lower panel of the cartridge receiver is correspondingly provided with a plurality of cylindrical slots having a same shape as the cylindrical protrusions; male and female electrical interfaces are respectively provided inside the cylindrical protrusions and cylindrical slots;

the cylindrical protrusions pass upward through the clamping port to clamp the cylindrical slots under an action of the elastic assembly, so as to power the laser element;

when the button assembly is moved backward, the clip-lock panel is driven to move obliquely downward along an axial direction of the cylindrical protrusions until the cylindrical protrusions disengage from the cylindrical slots;

when the button assembly is reset forward, the clip-lock panel is moved obliquely upward along the axial direction of the cylindrical protrusions under the action of the elastic assembly until the cylindrical protrusions engage with the cylindrical slots.

2. The exchangeable laser according to claim 1, wherein a back panel of the housing is provided with an optical interface at a position of the back panel horizontally corresponding to the insertion port, and the cartridge receiver is provided with an optical joint at a position corresponding to the optical-interface.

3. The exchangeable laser according to claim 1, wherein the clamping unit further comprises a clamping box, and the clamping box is fixed to the second accommodating space; a lower portion of the elastic assembly is fixed to a bottom of the clamping box;

when the clip-lock panel is moved up and down, the clip-lock panel is not completely detached from the clamping box;

a left side and right side of the clamping box are provided with a plurality of inclined guide rails having a same inclination degree as the axes of the cylindrical protrusions, and a left and right sides of the clip-lock panel are correspondingly provided with inclined guide channels.

4. The exchangeable laser according to claim 3, wherein the button assembly comprises a release button disposed at the front panel of the housing corresponding to the second accommodating space, and a frame connector arranged behind the release button;

a vertical strip-shaped slot is provided backside of the release button, and an inclined strip-shaped slot is provided frontside of the clip-lock panel; the vertical strip-shaped slot and the inclined strip-shaped slot have openings oriented perpendicular to left and right panels of the housing, respectively; an inclined direction of the inclined strip-shaped slot is perpendicular to the axes of the cylindrical protrusions;

an upper rod and lower rod of the frame connector respectively slide in the inclined strip-shaped slot and the vertical strip-shaped slot; a left rod and right rod of the frame connector are horizontally hinged to the left and right panels of the clamping box, respectively.

5. The exchangeable laser according to claim 1, wherein the clip-lock panel further comprises a buckle disposed on upper portions of the clip-lock panel and located in front of the cylindrical protrusions, and a slot is provided under the corresponding lower panel of the cartridge receiver;

when a back panel of the cartridge receiver is connected with the back panel of the housing, the buckle exactly engages with the slot, and the corresponding male and female electrical interfaces inside the cylindrical slots and the cylindrical protrusions are connected with each other.

6. The exchangeable laser according to claim 5, wherein the first accommodating space and the cartridge receiver have a same shape; the left panel and the right panel of the cartridge receiver are provided with horizontal positioning grooves, and a left panel and a right panel of the first accommodating space are provided correspondingly with horizontal positioning protrusions; and/or front portions of the left panel and the right panel of the cartridge receiver are provided with an anti-slip groove structure; the insertion port further comprises a plugging cartridge receiver groove corresponding to the anti-slip groove structure in front of the left panel and right panel of the housing.

7. The exchangeable laser according to claim 6, wherein an upper back portion of the cartridge receiver is further provided with a heat sink, and an upper panel of the housing is provided with a forced air cooling inlet at a position corresponding to a position of the heat sink; the left panel and/or the right panel of the housing are arranged with forced air cooling outlets.

8. The exchangeable laser according to claim 7, wherein the cylindrical protrusions are arrayed on upper surfaces of the clip-lock panel, the cylindrical slots are arrayed on the lower panel of the cartridge receiver corresponding to the array of the cylindrical protrusions.

9. The exchangeable laser according to claim 1, wherein the optical interface comprises a tapered cavity with a cone top at front and an axis extending rearward; a small cylindrical cavity is arranged extending horizontally forward from the cone top of the tapered cavity and is communication with the tapered cavity; a big cylindrical cavity is arranged extending horizontally backward from a cone bottom of the tapered cavity; a front side of the small cylindrical cavity is directly connected a laser output of the laser element, or connected to a laser output of the laser element through an optical fiber ferrule;

an optical joint corresponding to the optical interface comprises a tapered adapter having a same shape as the tapered cavity, and an external optical fiber disposed inside the tapered adapter; a front end of the external optical fiber is provided with an external optical fiber ferrule capable of inserting into the small cylindrical cavity; the external optical fiber ferrule is arranged at a front end of the tapered adapter; a cylindrical adapter with a same shape as the large cylindrical cavity is arranged extending forward from a back end of the tapered adapter; the cylindrical adapter extends to be flush with the back panel of the housing.

10. The exchangeable laser according to claim 9, wherein a top portion of the optical fiber ferrule has a lens; when the optical interface is docked with the optical joint, a distance between a front end face of an optical fiber of the external optical fiber ferrule and the lens is equal to a focal length of the lens.

11. The exchangeable laser according to claim 10, wherein the lens is a convex lens or a lenticular lens or a graded-index lens.

12. The exchangeable laser according to claim 9, wherein the tapered cavity has a taper angle of 45°.

13. An exchangeable laser array, comprising at least two of the exchangeable lasers according to claim 1, wherein in each of exchangeable lasers, a left side and right side of the housing are respectively provided with a horizontal guide channel array and a horizontal guide rail array.

14. The exchangeable laser array according to claim 13, wherein the exchangeable laser array further comprises a wavelength switcher, the wavelength switcher comprises a plurality of optical fiber input interfaces connected to optical interfaces of exchangeable lasers of the exchangeable laser array, one optical fiber output interface, a base, and a plurality of optical fiber plugs for connecting lasers that emit different wavelengths;

the base comprises a baseplate and a stationary shaft extending upward along a center of the baseplate; the stationary shaft is fixed with a drive gear and an optical fiber displacement disk that coincide with an axis of the stationary shaft from bottom to top;

each optical fiber plug comprises an optical fiber plugging rod, a driven gear assembly disposed at a periphery of the optical fiber plugging rod and used for meshing with the drive gear; one end of the optical fiber plugging rod is connected to one of the optical fiber input interfaces, and the other end of the optical fiber plugging rod is actively connected to the optical fiber output interface;

a plurality of optical fiber plugging ports for sleeving on the optical fiber plugging rod are axisymmetrically disposed on the optical fiber displacement disk at a radial periphery of the drive gear; a plurality of output ports for spirally connecting the optical fiber output interfaces are disposed on the baseplate vertically corresponding to the optical fiber plugging ports;

when the optical fiber plugging rod is located above the baseplate, the optical fiber displacement disk is rotated under an action of the drive gear and driven gear; when the optical fiber plugging rod is rotated to locate above the output port, the plurality of optical fiber plugging rods are moved up or down along the optical fiber plugging port under the action of the drive gear and driven gear, so as to pull out from the output port or insert into the optical fiber output port.

15. The exchangeable laser array according to claim 14, wherein the wavelength switcher further comprises a micro-switch device disposed above the optical fiber displacement disk; the micro-switch device comprises a micro-switchgear and a plurality of micro-switch elements; the micro-switchgear is provided with micro-switch positioning slots having a same angle as the optical fiber plug;

when the optical fiber displacement disk is rotated, a triggering unit of the micro-switch element is moved from a current micro-switch positioning slot to an adjacent micro-switch positioning slot, and at the same time, the optical fiber plug is moved from an upper position of one output port to an upper position of an adjacent output port.

16. The exchangeable laser array according to claim 14, wherein the driven gear of the optical fiber plug is connected to the optical fiber displacement disk through a bearing housing and a bearing of the bearing housing; the driven gear is connected to the optical fiber plugging rod through a screw-nut pair.

17. The exchangeable laser array according to claim 16, wherein a lower portion of the optical fiber plugging rod is provided with a vertical positioning slot matching with the positioning protrusion of the optical fiber plugging port; an upper portion of the vertical positioning slot is provided with a screw external thread matching with a screw internal thread of the driven gear.

18. The exchangeable laser array according to claim 17, wherein an upper portion of the screw external thread is provided with a spring and a spring positioning shoulder;

an upper portion of the spring positioning shoulder is the optical fiber ferrule for connecting to the optical fiber output interface.

19. The exchangeable laser array according to claim 17, wherein the screw internal thread of the driven gear is longer than the screw external thread of the optical fiber plugging rod; and the screw internal thread is only used for screwing inside the screw external thread; a thread stop structure is disposed at an end of the screw external thread for preventing the screw internal thread from being screwed out;

when a top of the screw external thread abuts against a top of the screw internal thread, and/or when a bottom of the vertical positioning slot abuts against a bottom of the positioning protrusion, a bottom of the optical fiber plugging rod is located at least above the baseplate.

* * * * *